(12) United States Patent
Ono et al.

(10) Patent No.: US 10,000,783 B2
(45) Date of Patent: Jun. 19, 2018

(54) STEVIOL GLUCOSYLTRANSFERASES AND GENES ENCODING THE SAME

(71) Applicant: SUNTORY HOLDINGS LIMITED, Osaka (JP)

(72) Inventors: Eiichiro Ono, Osaka (JP); Misa Ochiai, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days. days.

(21) Appl. No.: 14/383,698

(22) PCT Filed: Mar. 14, 2013

(86) PCT No.: PCT/JP2013/058189
§ 371 (c)(1),
(2) Date: Sep. 8, 2014

(87) PCT Pub. No.: WO2013/137487
PCT Pub. Date: Sep. 19, 2013

(65) Prior Publication Data
US 2015/0159188 A1 Jun. 11, 2015

(30) Foreign Application Priority Data
Mar. 16, 2012 (JP) ................. 2012-060473

(51) Int. Cl.
| | | |
|---|---|---|
| C07H 21/04 | (2006.01) |
| C12N 15/52 | (2006.01) |
| C12N 15/63 | (2006.01) |
| C12N 9/24 | (2006.01) |
| C12P 19/18 | (2006.01) |
| C12P 19/56 | (2006.01) |
| C07H 15/256 | (2006.01) |
| A61K 8/60 | (2006.01) |
| A61Q 19/00 | (2006.01) |
| C07H 1/00 | (2006.01) |
| C07H 21/00 | (2006.01) |
| C12N 9/10 | (2006.01) |
| A23L 27/30 | (2016.01) |
| A23L 33/13 | (2016.01) |

(52) U.S. Cl.
CPC ............ *C12P 19/56* (2013.01); *A23L 27/36* (2016.08); *A23L 33/13* (2016.08); *A61K 8/602* (2013.01); *A61Q 19/00* (2013.01); *C07H 1/00* (2013.01); *C07H 15/256* (2013.01); *C07H 21/00* (2013.01); *C12N 9/1051* (2013.01); *A23V 2002/00* (2013.01); *A61K 2800/10* (2013.01)

(58) Field of Classification Search
CPC ........ C12N 15/09; C12P 19/56; C12Y 204/00
USPC ................ 435/252.3, 320.1, 96; 536/23.2
See application file for complete search history.

(56) References Cited

U.S. PATENT DOCUMENTS

| 4,219,571 | A | 8/1980 | Miyake |
| 4,590,160 | A | 5/1986 | Nishihashi et al. |
| 9,243,273 | B2 | 1/2016 | Markosyan et al. |
| 9,562,251 | B2 | 2/2017 | Kishore et al. |
| 2008/0064063 | A1 | 3/2008 | Brandle et al. |
| 2010/0316782 | A1 | 12/2010 | Shi et al. |
| 2014/0017378 | A1 | 1/2014 | Purkayastha et al. |
| 2014/0030381 | A1 | 1/2014 | Markysyan |
| 2014/0357588 | A1 | 12/2014 | Markosyan et al. |
| 2015/0128306 | A1 | 5/2015 | Ono |
| 2016/0186225 | A1 | 6/2016 | Mikkelsen et al. |

FOREIGN PATENT DOCUMENTS

| EP | 1 897 951 | 12/2010 |
| EP | 2 832 858 | 2/2015 |
| JP | 05-255372 | 10/1993 |
| WO | 2011/153378 | 12/2011 |
| WO | 2013/022989 | 2/2013 |
| WO | 2013/176738 | 11/2013 |

OTHER PUBLICATIONS

Richman et al. "Functional genomics uncovers three glucosyltransferases involved in the synthesis of the major sweet glucosides of *Stevia rebaudiana*", The Plant Journal, vol. 41, No. 1, pp. 56-67 (2005).
Humphrey et al., "Spatial organization of four enzymes from *Stevia rebaudiana* that are involved in steviol glycoside synthesis", Plant Molecular Biology, vol. 61, No. 1-2, pp. 47-62 (2006).
Brandle et al., "Steviol glycoside biosynthesis", Phytochemistry, vol. 68, No. 14, pp. 1855-1863 (2007).
Kasai et al., "Sweet Diterpene-glycosides of Leaves of *Stevia rebaudiana* Bertoni Synthesis and Structure-Sweetness Relationship of Rebaudiosides-A, -D, -E and Their Related Glycosides", Journal of the Chemical Society of Japan, No. 5, pp. 726-735 (1981).
Mizutani et al., "Diversification of P450 Genes During Land Plant Evolution", Annu. Rev. Plant Biol., vol. 61, pp. 291-315 (2010).
Tanaka, "Improvement of Taste of Natural Sweeteners", Pure & Appl. Chem., vol. 69, No. 4, pp. 675-683 (1997).
International Search Report for PCT/JP2013/058189, dated Apr. 23, 2013.
U.S. Appl. No. 14/402,165 to Eiichiro Ono, filed Nov. 19, 2014.
U.S. Appl. No. 14/386,934 to Eiichiro Ono, filed Sep. 22, 2014.
Extended European Search Report issued in EP Patent Application No. 13761977.1, dated Oct. 12, 2015.

*Primary Examiner* — Robert B Mondesi
*Assistant Examiner* — Mohammad Y Meah
(74) *Attorney, Agent, or Firm* — Greenblum & Bernstein, P.L.C.

(57) ABSTRACT

Steviol glucosyltransferases and methods for producing steviol glycosides using the enzymes are provided.
The present invention provides steviol glucosyltransferases and methods for producing steviol glycosides using the enzymes. The invention also provides transformants into which steviol glucosyltransferase genes are introduced and methods for preparing the transformants.

11 Claims, 7 Drawing Sheets

Figure 1

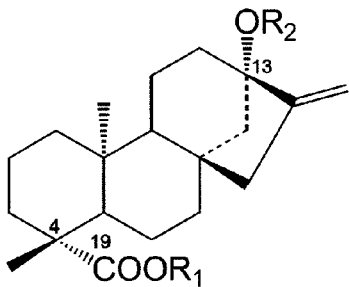

| Name | R₁ | R₂ |
|---|---|---|
| Steviol | H | H |
| Steviolmonoside | H | Glc |
| Steviolbioside | H | Glc-Glc(β2→1) |
| Dulcoside A | H | Glc-Rha(β2→1) |
| Rubusoside | Glc | Glc |
| Stevioside | Glc | Glc-Glc(β2→1) |
| Rebaudioside A | Glc | Glc-Glc(β2→1)<br>\|<br>Glc(β3→1) |
| Rebaudioside B | H | Glc-Glc(β2→1)<br>\|<br>Glc(β3→1) |
| Rebaudioside C (Dulcoside B) | Glc | Glc-Rha(β2→1)<br>\|<br>Glc(β3→1) |
| Rebaudioside D | Glc-Glc(β2→1) | Glc-Glc(β2→1)<br>\|<br>Glc(β3→1) |
| Rebaudioside E | Glc-Glc(β2→1) | Glc-Glc(β2→1) |
| Rebaudioside F | Glc | Glc-Xyl(β2→1)<br>\|<br>Glc(β3→1) |

Figure 6
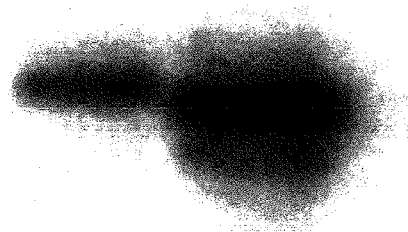

Figure 7

```
Sr_UGT91D1      MYNVTYHQNSKAMATSDSIVDDDRKQLHVATFPW
Sr_UGT91D-like3 MYNVTYHQNSKAMATSDSIVDDDRKQLHVATFPW
                                              *
Sr_UGT91D2e           MATSDSIVDDDRKQLHVATFPW
```

STEVIOL GLUCOSYLTRANSFERASES AND GENES ENCODING THE SAME

SEQUENCE LISTING

The instant application contains a Sequence Listing which has been submitted electronically in ASCII format and is hereby incorporated by reference in its entirety. Said ASCII copy, created on Jan. 2, 2015, is named P46224_SL.txt and is 61,828 bytes in size.

TECHNICAL FIELD

The present invention relates to a protein having an activity of synthesizing steviol glycosides and a polynucleotide encoding the protein, a method for producing steviol glycosides using the protein, a transformant highly expressing steviol glucosyltransferases, steviol glycosides produced by the method and use thereof.

BACKGROUND ART

The leaves of *Stevia rebaudiana* contain a secondary metabolite called steviol, which is a member of diterpenoids. Steviol glycosides elicit a sweet taste that are up to about 300 times the sweetness of sugar, and have been used as non-caloric sweeteners in the food industry. Obesity is globally increasing as a serious social problem, and demand for non-caloric sweeteners is growing every day from viewpoints of promoting health and reducing medical expenses. Currently, Aspartame and Acesulfame Potassium, which are artificially synthesized amino acid derivatives, are used as artificial sweeteners. However, it is expected that naturally occurring non-caloric sweeteners like steviol glycosides are more likely to enjoy public acceptance.

Steviol contained in the leaves of *stevia* is modified with sugars finally to a glycoside called rebaudioside A with four glucose moieties attached (FIG. 1). Its precursor steviol triglycoside, stevioside, is most abundant quantitatively, and rebaudioside A and stevioside are the main components of sweetness in *stevia*. In addition to them, the presence of glycosides considered to be reaction intermediates and analogs with different sugars are known.

Enzyme genes encoding biosynthesis of rebaudioside A have been isolated through an expressed sequence tag (EST) analysis of *stevia* (Non-Patent Documents 1 and 2, Patent Document 1). Steviol is produced through hydroxylation at position 13 of ent-kaurenoic acid, i.e., a precursor of plant hormone diterpenoid, gibberellins, by cytochrome P450 enzyme ent-kaurenoic acid, 13-hydroxylase (EK13H) (FIG. 2) (Non-Patent Document 3, Patent Document 1). The 13-hydroxy group of steviol is first glycosylated (monoglucosylation) by UGT85C2 to produce steviolmonoside. The position 2 of the glucose at position 13 of steviolmonoside is further glucosylated to form steviolbioside, or the carboxyl group at position 19 of steviolmonoside is glucosylated to form a steviol diglycoside called rubusoside. Steviolbioside or rubusoside thus produced is considered to undergo further glycosylation to form steviol glycosides such as stevioside and rebaudioside A. UGT74G1 and UGT76G1 are known as enzyme genes involved in formation of steviol glycosides.

UGT74G1 is known to catalyze glucosylation of the position 19 of steviolmonoside (Non-Patent Document 1). UGT74G1 also catalyzes glucosylation of steviolbioside to produce stevioside which is a steviol triglycoside. The content of stevioside is most abundant in the leaves of *stevia*; stevioside is known to be approximately 250 to 300 times sweeter than sugar. This stevioside is further glucosylated by UGT76G1 to produce steviol tetraglycoside, rebaudioside A, which is the sweetest (350 to 450 times sweeter than sugar) and reportedly has a favorable quality of taste.

It is reported on steviol glycosides that addition of branched sugars especially to the glucose at position 13 results in improved quality of taste and sweetness (Non-Patent Document 4, Patent Document 2). It is thus considered that glycosidases that catalyze these reactions are important enzymes to determine sweetness qualities of *stevia*.

In the previous study (Non-Patent Document 2), several types of glucosyltransferases (UGT) are reported by the EST analysis of *stevia* leaves. However, detailed enzyme activities of all these enzymes have not been fully investigated. Also, a homologous protein of UGT91D1 is reported only for the isolation of an truncated sequence (Patent Document 3).

PRIOR ART DOCUMENTS

Patent Documents

[Patent Document 1] EP 1 897 951 B1
[Patent Document 2] Japanese Patent Laid-Open Application No. H05-255372
[Patent Document 3] WO2011/153378A1

Non-Patent Documents

[Non-Patent Document 1] Brandle and Telmer (2007) Phytochemistry 68, 1855-1863
[Non-Patent Document 2] Richman et al (2005) Plant J. 41, 56-67
[Non-Patent Document 3] Mizutani and Ohta (2010) Annu. Rev. Plant Biol. 61, 291-315
[Non-Patent Document 4] Kasai et al., (1981) Bulletin of the Chemical Society of Japan 5, 726-735

DISCLOSURE OF THE INVENTION

Problems to be Solved by the Invention

As a result of extensive studies, the present inventors have succeeded in identifying enzymes that catalyze glycosylation of the glucose at position 13 of steviol glycosides in *stevia* and genes encoding the enzymes. The present invention is based on the finding above.

Means for Solving the Problem

That is, the present invention is described as follows.
[1] A protein according to any one selected from the group consisting of (a) to (c) below:
(a) a protein consisting of the amino acid sequences of SEQ ID NO: 2;
(b) a protein consisting of an amino acid sequence wherein 1 to 48 amino acids are deleted, substituted, inserted and/or added in the amino acid sequence of SEQ ID NO: 2, and having an activity of adding a sugar molecule to the glucose at position 13 of a compound represented by general formula (I) below; and,
(c) a protein having an amino acid sequence having at least 90% sequence identity with the amino acid sequence of SEQ ID NO: 2, and having an activity of adding a sugar molecule to the glucose at position 13 of a compound represented by general formula (I) below:

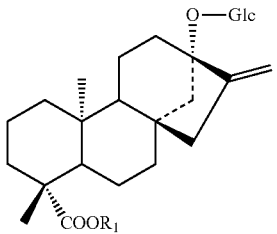

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

[2] The protein according to [1] above, wherein the sugar molecule is a hexose.

[3] The protein according to [1] above, wherein the sugar molecule is one selected from the group consisting of glucose, mannose and galactose.

[4] The protein according to [1] above, wherein said $R_1$ is H or the sugar residue which is a glucose monomer or a glucose dimer.

[5] The protein according to [1] above, wherein the compound is steviolmonoside or rubusoside.

[6] A polynucleotide according to any one selected from the group consisting of (a) to (e) below:

(a) a polynucleotide comprising the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 48 amino acids are deleted, substituted, inserted and/or added in the amino acid sequence of SEQ ID NO: 2, and having an activity of adding a sugar molecule to the glucose at position 13 of a compound represented by general formula (I) below;

(d) a polynucleotide encoding a protein having an amino acid sequence having at least 90% sequence identity with the amino acid sequence of SEQ ID NO: 2, and having an activity of adding a sugar molecule to the glucose at position 13 of a compound represented by general formula (I) below: and, (e) a polynucleotide that hybridizes under highly stringent conditions with a polynucleotide consisting of a nucleotide sequence complementary to the nucleotide sequence of SEQ ID NO: 1 and encodes a protein having an activity of adding a sugar molecule to the glucose at position 13 of a compound represented by general formula (I) below:

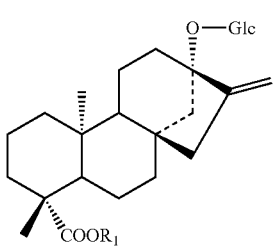

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

[7] The polynucleotide according to [6] above, wherein the sugar molecule is one selected from the group consisting of glucose, mannose and galactose.

[8] The polynucleotide according to [6] above, wherein said $R_1$ is H or the sugar residue which is a glucose monomer or a glucose dimer.

[9] The polynucleotide according to [6] above, wherein the compound is steviolmonoside or rubusoside.

[10] A non-human transformant, into which the polynucleotide according to [6] above is introduced.

[11] The transformant according to [10] above, wherein the polynucleotide is inserted into an expression vector.

[12] The transformant according to [10] above, which is a microorganism or a plant body.

[13] An extract from the transformant according to [10] above.

[14] A food, pharmaceutical composition or industrial material comprising the extract according to [13] above.

[15] A method for producing a protein, which comprises culturing the non-human transformant according to [10] above, wherein the protein has an activity of adding a sugar molecule to the glucose at position 13 of a compound represented by general formula (I) below:

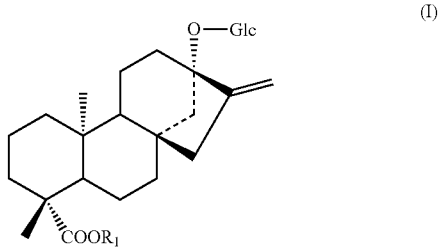

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

[16] A method for producing a steviol glycoside, which comprises using the non-human transformant according to [10] above.

[17] The method according to [16] above, wherein the steviol glycoside is steviolbioside, stevioside, rebaudioside A, rebaudioside B, rebaudioside C, rebaudioside D, rebaudioside E, rebaudioside F, or a combination thereof.

[18] The method according to [16] above, wherein the non-human transformant expresses at least one gene selected from the group consisting of UGT85C2 gene, UGT74G1 gene and UGT76G1 gene, and the steviol glycosides produced are steviolbioside, rebaudioside A, stevioside and rebaudioside B.

[19] A method for producing a steviol glycoside, which comprises the step of reacting the protein according to [1] above with a UDP-sugar and a compound represented by general formula (I) below:

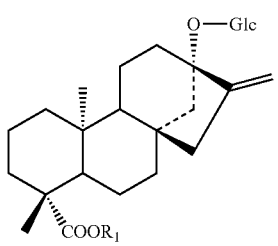

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

[20] The method according to [19] above, wherein the sugar in the UDP-sugar is glucose.

[21] The method according to [19] above, wherein the steviol glycoside is steviolbioside, stevioside, rebaudioside A, rebaudioside B, rebaudioside C, rebaudioside D, rebaudioside E, rebaudioside F, or a combination thereof.

Effects of the Invention

By using the protein of the present invention and the polynucleotide encoding the same, steviol glycosides (e.g., steviolbioside and stevioside, etc.) can be produced with a high efficiency. The transformants of the present invention have a high content of steviol glycosides (e.g., steviolbioside and stevioside, etc.) and steviol glycosides (e.g., steviolbioside and stevioside, etc.) can be efficiently extracted and purified from these transformants.

By co-expression the protein of the present invention and the polynucleotide encoding the protein together with other steviol glucosyltransferases or polynucleotides encoding the enzymes simultaneously in the same host cell, more highly glycosylated steviol glycosides (e.g., rebaudioside A and rebaudioside B, etc.) can be prepared.

BRIEF DESCRIPTION OF DRAWINGS

FIG. 1 shows the names and structures of steviol glycosides. In FIG. 1, "Glc-Glc (β2→1)" denotes that "Glc-Glc" binds through β2,1 glycoside bond, and "Glc-Glc (β3→1)" denotes that "Glc-Glc" binds through β3,1 glycoside bond.

FIG. 6 shows the expression of recombinant proteins. The expressions of UGT91D-like3 and UGT91D2e in forms of HisTag fusion proteins were detected, respectively, by Western blotting for the recombinant proteins. UGT91D2e is short by the 12 amino acids and the band is detected at a slightly smaller size than UGT91D-like3.

FIG. 7 shows the alignment of the partial N-terminal sequences of UGT91D homologous enzymes (SEQ ID NO: 35, SEQ ID NO: 35, and SEQ ID NO: 36, respectively, in order of appearance), in which the amino acid sequences of UGT91D1, UGT91D-like3 and UGT91D2e are shown in the order from the top. Asterisk (*) denotes the position corresponding to histidine residue (VvGT1_His20) of glycosyltransferase VvGT1 from grape, which residue is considered to be essential for the catalytic activity thereof.

Figure 2:
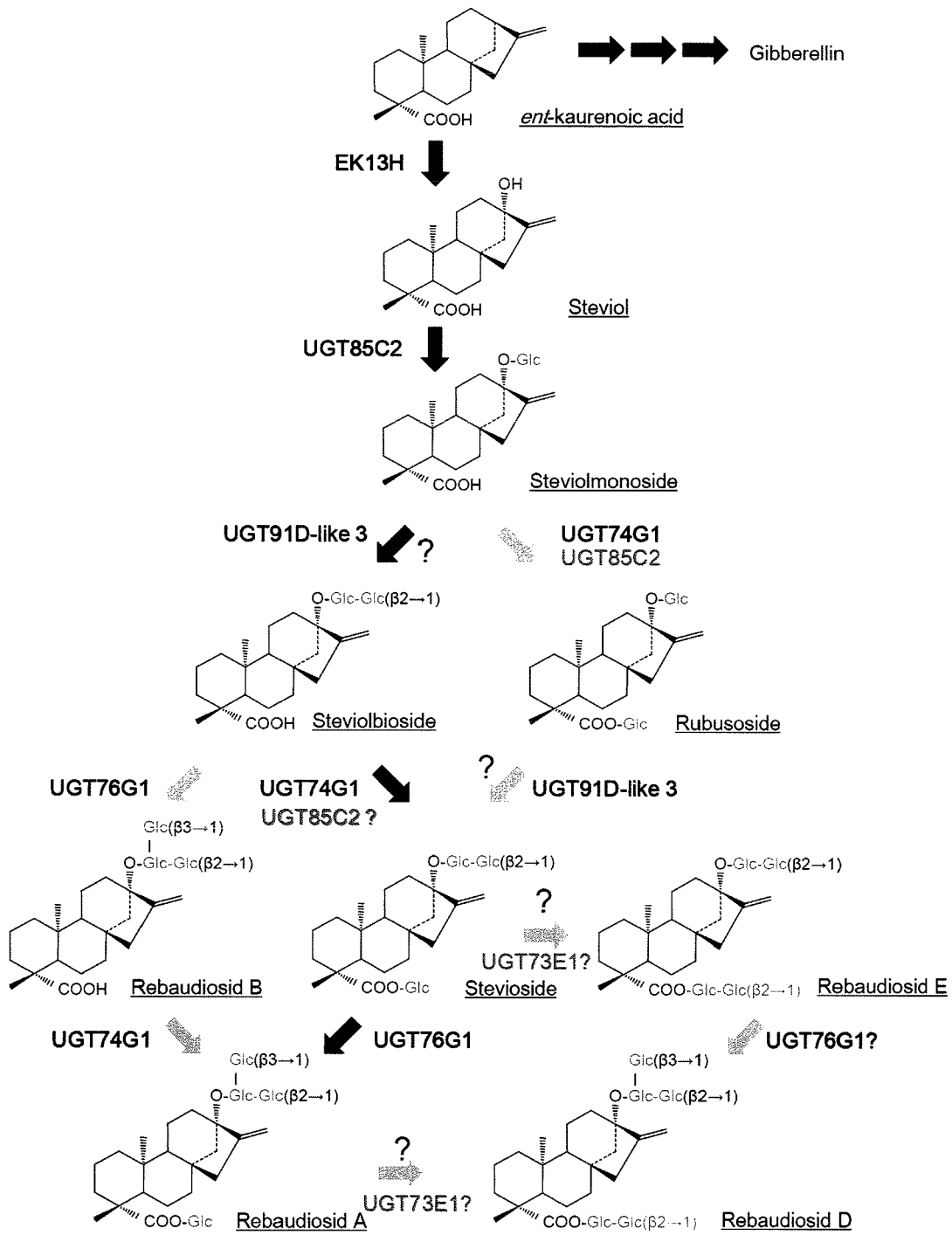
FIG. 2 shows presumed biosynthetic pathway of steviol glycosides.

Hereinafter, the present invention is described in detail. The embodiments described below are presented by way of example merely to describe the invention but not limited only to the following embodiments. The present invention may be implemented in various ways without departing from the gist of the invention.

All of the publications, published patent applications, patents and other patent documents cited in the specification are herein incorporated by reference in their entirety. The specification hereby incorporates by reference the contents of the specification and drawings in the Japanese Patent Application (No. 2012-60473) filed Mar. 16, 2012, from which the priority was claimed.

The present inventors have elucidated for the first time that the enzyme protein responsible for glycosylation to the glucose at position 13 in steviol glycosides is UGT91D-like3.

The CDS sequence and putative amino acid sequence of UGT91D-like3 are SEQ ID NOS: 1 and 2, respectively. The polynucleotides and enzymes described above may be obtained by the methods described in EXAMPLES later described, known genetic engineering techniques, known methods for synthesis, and so on.

1. Steviol Glucosyltransferase

The present invention provides the protein according to any one selected from the group consisting of (a) to (c) below (hereinafter referred to as the "protein of the present invention"):

(a) a protein consisting of the amino acid sequences of SEQ ID NO: 2;

(b) a protein consisting of an amino acid sequence wherein 1 to 48 amino acids are deleted, substituted, inserted and/or added in the amino acid sequence of SEQ ID NO: 2, and having an activity of adding a sugar molecule to the glucose at position 13 of a compound represented by general formula (I) below; and, (c) a protein having an amino acid sequence having at least 90% sequence identity with the amino acid sequence of SEQ ID NO: 2, and having an activity of adding a sugar molecule to the glucose at position 13 of a compound represented by general formula (I) below:

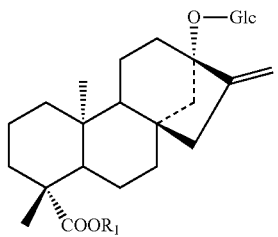

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

The proteins described in (b) or (c) above are typically mutants of the naturally occurring polypeptide of SEQ ID NO: 2 and also include those proteins which may be artificially obtained using site-directed mutagenesis described in, e.g., "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, "the protein consisting of an amino acid sequence wherein 1 to 48 amino acids are deleted, substituted, inserted and/or added in the amino acid sequence of SEQ ID NO: 2, and having an activity of adding a sugar molecule to the glucose at position 13 of a compound represented by general formula (I)" includes proteins containing an amino acid sequence wherein, e.g., 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or one amino acid is/are deleted, substituted, inserted and/or added in the amino acid sequence of SEQ ID NO: 2, and having the activity of adding a sugar molecule to the glucose at position 13 of the compound represented by general formula (I). In general, the number of deletions, substitutions, insertions, and/or additions is preferably smaller.

Such proteins include proteins having an amino acid sequence having the identity of approximately 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, with the amino acid sequence of SEQ ID NO: 2, and having the activity of adding a sugar molecule to the glucose at position 13 of the compound represented by general formula (I). As the identity percentage described above is higher, the protein is preferred in general.

As used herein, "the activity of adding a sugar molecule to the glucose at position 13 of the compound represented by general formula (I)" is intended to mean the activity of adding sugars to the glucose at position 13 of the compound represented by general formula (I) below.

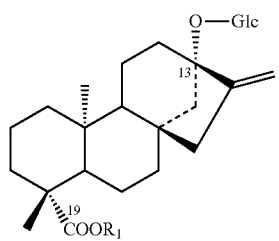

(I)

In general formula (I), Glc represents a glucose residue. $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl or a ($C_3$-$C_{10}$ cycloalkyl) $C_1$-$C_{10}$ alkyl, or a sugar residue, in general formula (I).

As used herein, the "$C_1$-$C_{20}$ alkyl" is preferably a $C_1$-$C_{10}$ alkyl, and more preferably a $C_1$-$C_6$ alkyl. The alkyl group includes, but not limited to, methyl, ethyl, propyl, isopropyl, n-butyl, sec-butyl, tert-butyl, pentyl, hexyl, dodecanyl, etc.

As used herein, the "$C_2$-$C_{20}$ alkenyl" is preferably a $C_2$-$C_{10}$ alkenyl, and more preferably a $C_2$-$C_6$ alkenyl. The alkenyl group includes, but not limited to, vinyl, allyl, propenyl, isopropenyl, 2-methyl-1-propenyl, 2-methylallyl, 2-butenyl, etc.

As used herein, the "$C_2$-$C_{20}$ alkynyl" is preferably a $C_2$-$C_{10}$ alkynyl, and more preferably a $C_2$-$C_6$ alkynyl. The alkynyl group includes, but not limited to, ethynyl, 2-propynyl, 2-butynyl, etc.

As used herein, the "$C_4$-$C_{20}$ alkyldienyl" is preferably a $C_4$-$C_{10}$ alkyldienyl, and more preferably a $C_4$-$C_6$ alkyldienyl. The alkyldienyl group includes, but not limited to, 1,3-butadienyl, etc.

As used herein, the "$C_6$-$C_{18}$ aryl" is preferably a $C_6$-$C_{10}$ aryl. The aryl group includes, but not limited to, phenyl, 1-naphthyl, 2-naphthyl, indenyl, biphenylyl, anthryl, phenanthryl, etc.

As used herein, the "$C_6$-$C_{20}$ alkylaryl" is preferably a $C_6$-$C_{12}$ alkylaryl. The alkylaryl group includes, but not limited to, o-tolyl, m-tolyl, p-tolyl, 2,3-xylyl, 2,4-xylyl, 2,5-xylyl, o-cumenyl, m-cumenyl, p-cumenyl, mesityl, etc.

As used herein, the "$C_6$-$C_{20}$ arylalkyl" is preferably a $C_6$-$C_{12}$ arylalkyl. The arylalkyl group includes, but not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.

As used herein, the "$C_4$-$C_{20}$ cycloalkyl" is preferably a $C_4$-$C_{10}$ cycloalkyl. The cycloalkyl group includes, but not limited to, cyclopropyl, cyclobutyl, cyclopentyl, cyclohexyl, etc.

As used herein, the "$C_4$-$C_{20}$ cycloalkenyl" is preferably a $C_4$-$C_{10}$ cycloalkenyl. The cycloalkenyl group includes, but not limited to, cyclopropenyl, cyclobutenyl, 2-cyclopenten-1-yl, 2-cyclohexen-1-yl, 3-cyclohexen-1-yl, etc.

As used herein, examples of the "($C_3$-$C_{10}$ cycloalkyl) $C_1$-$C_{10}$ alkyl" include methylcyclopropyl, ethylcyclopropyl, methylcyclobutyl, ethylcyclopentyl, methylcyclohexyl, etc.

As used herein, the "sugar residue" may include, but not limited to, a residue of one or more sugars including a pentose, a hexose or a combination thereof (excluding xylose, rhamnose or a combination thereof).

Examples of pentose (excluding xylose, rhamnose or a combination thereof) are ribose, arabinose and lyxose, and examples of the hexose are allose, altrose, glucose, mannose, gulose, idose, galactose and talose.

Preferably, the "sugar residue" refers to a residue of sugar consisting of at least one hexose unit, and more preferably, a glucose monomer (–Glc) or a glucose dimer (–Glc-Glc). In a sugar residue of the glucose dimer, glucose is linked to each other preferably through a β2, 1 glycoside bond.

The compound of general formula (I) is preferably stebiolmonoside or rubusoside.

The sugar molecule added by the protein of the present invention to the glucose at position 13 of the compound represented by general formula (I) may include, but not limited to, sugar molecules consisting of at least one pentose, hexose or a combination thereof (excluding xylose, rhamnose or a combination thereof). Examples of the pentose and hexose are the same as described above. The sugar molecule described above is preferably a hexose, and more preferably, a hexose selected from the group consisting of glucose, mannose and galactose. The sugar molecule above is most preferably glucose.

The activity of adding the sugar molecule to the glucose at position 13 of the compound represented by general formula (I) can be verified as follows. 1-500 ng (preferably, 50-200 ng, most preferably, 100 ng) of a test protein, 1-1000 µM (preferably, 100-700 µM, most preferably, 500 µM) of UDP sugar (e.g., UDP-glucose) and 1-500 µM (preferably, 100-500 µM, most preferably, 250 µM) of substrate compound (compound of general formula (I)) are incubated in a buffer (e.g., sodium phosphate buffer or potassium phosphate buffer) in the neutral pH range of pH 6.0-8.0 at a temperature of 20-40° C. for 10 minutes to 2 hours. Then the substrate compound above is purified and the monoterpene purified is analyzed by known means such as the LC-MS analysis (Liquid Chromatography-Mass Spectrometry), etc.

In the case that the sugar molecule attached to the glucose at position 13 of the compound represented by general formula (I) is detected as a result of the LC-MS analysis, the test protein described above is considered to have the activity of adding the sugar molecule to the glucose at position 13 of the compound represented by general formula (I).

In general, the glycosylation reaction is completed approximately in a minute to 12 hours.

The deletion, substitution, insertion and/or addition of one or more amino acid residues in an amino acid sequence of the protein of the invention is intended mean that one or a plurality of amino acid residues are deleted, substituted, inserted and/or added at one or a plurality of positions in the same amino acid sequence. Two or more types of deletions, substitutions, insertions and additions may occur at the same time.

Examples of the amino acid residues which are mutually substitutable are given below. Amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may be obtained by expressing a polynucleotide (c f, "the polynucleotide of the present invention" later described) encoding the protein in an appropriate host cell. The protein may also be produced by chemical synthesis methods such as the Fmoc method (fluorenylmethyloxycarbonyl method), the tBoc method (t-butyloxycarbonyl method), etc. In addition, peptide synthesizers available from Advanced Automation Peptide Protein Technologies, Perkin Elmer, Protein Technology Instrument, PerSeptive, Applied Biosystems, SHIMADZU Corp., etc. may also be used for the chemical synthesis.

2. Method for Producing Steviol Glycosides

Steviol glycosides can be produced easily and abundantly by using the activity of the protein of the present invention to add the sugar molecule to the glucose at position 13 of the compound represented by general formula (I).

In another embodiment, the present invention provides Method 1 for producing steviol glycosides, which comprises reacting the protein of the present invention and the compound represented by general formula (I) below to add a sugar molecule to the glucose at position 13 of the compound represented by general formula (I).

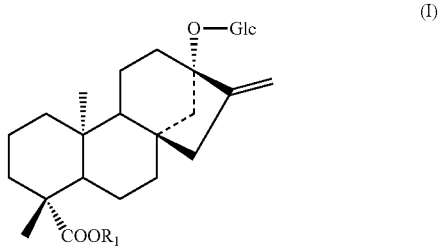

In general formula (I), Glc and $R_1$ have the same significance as defined above. Preferably, the compound of general formula (I) is steviolmonoside or rubusoside.

As used herein, the term "UDP-sugar" refers to uridine diphosphate (Uridine DiPhosphate: UDP)-bound sugar. In the UDP-sugar, preferred examples of the sugar moiety include sugars consisting of at least one pentose (excluding xylose), hexose or a combination thereof. Examples of the pentose (excluding xylose) and hexose are the same as those discussed above. The UDP-sugar is preferably UDP-hexose, and more preferably, a hexose selected from the group consisting of glucose, mannose and galactose. The UDP-sugar described above is most preferably UDP-glucose.

Method 1 for producing the steviol glycoside in accordance with the present invention comprises the step of reacting the protein of the present invention, the UDP-sugar and the compound represented by general formula (I) to add a sugar molecule to the glucose at position 13 of the compound represented by general formula (I). Method 1 of the present invention may further include the step of purifying the steviol glycoside produced in the step above.

Examples of the steviol glycoside produced by Method 1 include, but not limited to, steviolbioside, stevioside, rebaudioside A, rebaudioside B, rebaudioside C, rebaudioside D, rebaudioside E, rebaudioside F, or a combination thereof.

The steviol glycoside produced may be purified by known procedures including extraction with an appropriate solvent (an aqueous solvent such as water, etc., or an organic solvent such as alcohol, ether, acetone, etc.), a gradient with ethyl acetate or other organic solvent: water, high performance liquid chromatography (HPLC), gas chromatography, time-of-flight mass spectrometry (TOF-MS), ultra high performance liquid chromatography (UPLC), etc.

3. Non-Human Transformant with High Steviol Glycoside Level

The steviol glycoside may also be produced in cells from bacteria (*Escherichia coli*, yeast, etc.), plants, insects, mammals except human, etc., using the protein of the present invention. This is because the protein of the present invention is an enzyme derived from *stevia* or a variant thereof and thus expected to retain its high activity even under intracellular environment. In this case, the steviol glycoside can be produced by introducing a polynucleotide encoding the protein of the present invention (cf., "the polynucleotide of the present invention" as described later) into host cells derived from bacteria, plants, insects, mammals except human, etc. to express the protein of the present invention and reacting the protein of the present invention, the UDP-sugar present in the cells above and the compound represented by general formula (I).

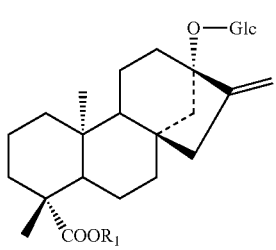

Therefore, the present invention provides non-human transformants, into which a polynucleotide according to any one selected from the group consisting of (a) to (e) below (hereinafter referred to as the "polynucleotide of the present invention") is introduced:

(a) a polynucleotide comprising the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 48 amino acids are deleted, substituted, inserted and/or added in the amino acid sequence of SEQ ID NO: 2, and having an activity of adding a sugar molecule to the glucose at position 13 of a compound represented by general formula (I) below;

(d) a polynucleotide encoding a protein having an amino acid sequence having at least 90% sequence identity with the amino acid sequence of SEQ ID NO: 2, and having an activity of adding a sugar molecule to the glucose at position 13 of a compound represented by general formula (I) below: and, (e) a polynucleotide that hybridizes under highly stringent conditions with a polynucleotide consisting of a nucleotide sequence complementary to the nucleotide sequence of SEQ ID NO: 1 and encodes a protein having an activity of adding a sugar molecule to the glucose at position 13 of a compound represented by general formula (I).

The definition and specific examples of general formula (I) are the same as already stated above, and the definition and specific examples of the sugar molecule added to the position 13 of the compound represented by general formula (I) are also the same as described above.

As used herein, the term "polynucleotide" is intended to mean a DNA or RNA.

As used herein, the term "polynucleotide which hybridizes under highly stringent" refers to, e.g., a polynucleotide consisting of a nucleotide sequence complementary to the nucleotide sequence of SEQ ID NO: 1, or a polynucleotide obtained by the colony hybridization method, plaque hybridization method, Southern hybridization method or the like, using as a probe the whole or part of a polynucleotide consisting of the nucleotide sequence encoding the amino acid sequence of SEQ ID NO: 2. For the methods of hybridization, there are used the methods described in, e.g., "Sambrook & Russell, Molecular Cloning; A Laboratory Manual Vol. 3, Cold Spring Harbor, Laboratory Press 2001" and "Ausubel, Current Protocols in Molecular Biology, John Wiley & Sons 1987-1997," etc.

As used herein, the term "highly stringent conditions" are conditions, for example, (1) 5×SSC, 5×Denhardt's solution, 0.5% SDS and 50% formamide at 50° C., (2) 0.2×SSC and 0.1% SDS at 60° C., (3) 0.2×SSC and 0.1% SDS at 62° C., (4) 0.2×SSC and 0.1% SDS at 65° C., or (5) 0.1×SSC and 0.1% SDS at 65° C., but not limited thereto. Under these conditions, a DNA with higher sequence identity may be expected to be obtained efficiently at higher temperatures, although multiple factors are involved in hybridization stringency including temperature, probe concentration, probe length, ionic strength, time, salt concentration and others, and those skilled in the art may appropriately select these factors to achieve similar stringency.

When commercially available kits are used for hybridization, for example, an Alkphos Direct Labeling and Detection System (GE Healthcare) may be used. In this case, according to the attached protocol, after incubation with a labeled probe overnight, the membrane is washed with a primary wash buffer containing 0.1% (w/v) SDS at 55 to 60° C., thereby detecting hybridized DNA. Alternatively, in producing a probe based on the nucleotide sequence complementary to the nucleotide sequence of SEQ ID NO: 1 or on the entire or part of the nucleotide sequence encoding the amino acid sequence of SEQ ID NO: 2, hybridization can be detected with a DIG Nucleic Acid Detection Kit (Roche Diagnostics) when the probe is labeled with digoxigenin (DIG) using a commercially available reagent (e.g., a PCR Labeling Mix (Roche Diagnostics), etc.).

In addition to those described above, other polynucleotides that can be hybridized include DNAs having 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity with the DNA of SEQ ID NO: 1, or the DNA encoding the amino acid sequence of SEQ ID NO: 2, as calculated by homology search software, such as FASTA and BLAST using default parameters.

Identity between amino acid sequences or nucleotide sequences may be determined using FASTA (Science 227 (4693): 1435-1441, (1985)), algorithm BLAST (Basic Local Alignment Search Tool) by Karlin and Altschul (Proc. Natl. Acad. Sci. USA, 87: 2264-2268, 1990; Proc. Nail Acad. Sci. USA, 90: 5873, 1993). Programs called blastn, blastx, blastp, tblastn and tblastx based on the BLAST algorithm have been developed (Altschul S. F. et al., J. Mol. Biol. 215: 403, 1990). When a nucleotide sequence is sequenced using blastn, the parameters are, for example, score=100 and wordlength=12. When an amino acid sequence is sequenced using blastp, the parameters are, for example, score=50 and wordlength=3. When BLAST and Gapped BLAST programs are used, default parameters for each of the programs are employed.

The polynucleotides of the present invention described above can be acquired by known genetic engineering techniques, known methods for synthesis, and so on.

The polynucleotides of the present invention is introduced into a host, preferably, in such a state that it is inserted into an appropriate expression vector.

The appropriate vector is generally constructed to contain an expression cassette comprising:

(i) a promoter that can be transcribed in a host cell;

(ii) any of the polynucleotides of the present invention that is linked to the promoter; and, (iii) an expression cassette comprising as a component a signal that functions in the host cell with respect to the transcription termination and polyadenylation of RNA molecule.

To construct the expression vector, procedures using a plasmid, phage or cosmid are used but are not particularly limited thereto.

Vectors are not particularly limited to any specific type, and those capable of expressing in a host cell can be suitably chosen. That is, a suitable promoter sequence may be chosen depending upon the type of a host cell to reliably express the polynucleotide of the invention, and a vector obtained by incorporating this sequence and the polynucleotide of the present invention into various plasmids or the like may be used as an expression vector.

The expression vector of the present invention contains an expression control region (e.g., a promoter, a terminator, and/or a replication origin, etc.) depending on the type of a host to be introduced. A conventional promoter (e.g., trc promoter, tac promoter, lac promoter, etc.) is used as the promoter for a bacterial expression vector. As the promoter for yeast, there are used, for example, GAL1 promoter, GAL10 promoter, glyceraldehyde 3-phosphate dehydrogenase promoter, PH05 promoter, etc. As the promoter for fungi there are used, for example, amylase, trpC, etc. Furthermore, examples of the promoter for expressing the gene of interest in plant cells include cauliflower mosaic virus 35S RNA promoter, rd29A gene promoter, rbcS promoter, mac-1 promoter wherein an enhancer sequence of the cauliflower mosaic virus 35S RNA promoter above is added to the 5' end of mannopine synthetase promoter sequence from *Agrobacterium*, etc. Viral promoter (e.g., SV40 early promoter, SV40 late promoter, etc.) are used as the promoter for animal-derived host cells.

Preferably, the expression vector contains at least one selection marker. As such a selection marker, there may be used auxotrophic markers (ura5, niaD, TRP 1, URA3, HIS3, LEU2), chemical-resistant markers (hygromycin, zeocin), genecitin-resistant gene (G418r), copper-resistant gene (CUP 1) (Marin et al., Proc. Natl. Acad. Sci. USA, 81, p. 337 1984), cerulenin-resistant gene (fas2m, PDR4) (Junji Inokoshi, et al., Biochemistry, 64, p. 660, 1992; and Hussain et al., Gene, 101: p. 149, 1991, respectively), etc.

A method of preparing (method of producing) the transformant of the present invention is not particularly limited and includes, e.g., a method which comprises introducing the expression vector bearing the polynucleotide of the present invention into a host for transformation.

The transformant of the present invention is expected to produce the steviol glycoside with a high efficiency. Host cells used for transformation are not particularly limited and various cells can be advantageously used. Examples of the host cells are bacteria such as *Escherichia coli*, etc., yeast (*Saccharomyces cerevisiae, Schizosaccharomyces pombe*, plant cells, animal cells except human, etc.

Host cells are preferably host cells capable of producing the compound represented by general formula (I). Herein, host cells are not limited to those capable of producing the compound represented by general formula (I) in a natural state, and may be those genetically engineered by known genes so as to be able to produce the compound represented by general formula (I).

The genes encoding the enzymes that contribute to synthesis of the compound represented by general formula (I) include known genes such as EK13H, UGT74G1 and UGT76G1 (Non-Patent Document 2), but are not limited thereto.

In the case that the host cell is incapable of producing the compound represented by general formula (I), the compound of general formula (I) or a plant extract containing the compound may be added as a substrate to the culture system of the transformants obtained by introducing the gene of the invention in the host cell, and thus, the steviol glycoside can be produced without introducing the gene encoding the enzyme that contributes to synthesis of the compound represented by general formula (I).

Furthermore, the polynucleotide of the present invention is expressed in the host cell into which genes encoding the glucosyltransferases responsible for a series of glycoside synthesis from steviol to rebaudioside A have been introduced, thereby highly glycosylated steviol glycosides (e.g., steviolbioside, rebaudioside A, stevioside, rebaudioside B, etc.) can be produced. Examples of the glucosyltransferase involved in a series of glycoside synthesis from steviol to rebaudioside A include UGT85C2 (CDS sequence: SEQ ID NO: 5, amino acid sequence: SEQ ID NO: 6), UGT74G1 (CDS sequence: SEQ ID NO: 7, amino acid sequence: SEQ ID NO: 8), UGT76G1 (CDS sequence: SEQ ID NO: 9, amino acid sequence: SEQ ID NO: 10), etc.

Culture media and conditions suitable for the host cells above are well known in the art. The organism to be transformed is not particularly limited, and includes various microorganisms, plants and animals other than human, which given as examples of the host cells above.

For transformation of host cells, there may be used generally known methods. The transformation can be performed by the electroporation method (Mackenzie D. A. et al., Appl. Environ. Microbiol., 66, 4655-4661, 2000), the particle delivery method (JPA 2005-287403), the spheroplast method (Proc. Natl. Acad. Sci. USA, 75 p. 1929 (1978)), the lithium acetate method (the methods described in J. Bacteriology, 153 p. 163 (1983)), Methods in yeast genetics, 2000 Edition: A Cold Spring Harbor Laboratory Course Manual, etc.), but is not limited thereto.

In addition, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc., for general molecular biological techniques.

The steviol glycoside can be produced by the transformant through incubation of the transformant thus obtained. As described above, the compound of general formula (I) or a plant extract containing the compound may also be added the culture system of the transformant as a substrate to promote production of the steviol glycoside. The steviol glycoside accumulated may be extracted and purified to give the steviol glycoside of interest.

Thus, the present invention provides Method 2 for producing the steviol glycoside, which comprises using the transformant of the present invention. Suitable culture media and conditions are well known in the art. The procedures for extraction and purification of the steviol glycoside are already described.

The steviol glycoside is not particularly limited, and preferably may be one selected from the group consisting of steviolbioside, stevioside, rebaudioside A, rebaudioside B, rebaudioside C, rebaudioside D, rebaudioside E, rebaudioside F, or a combination thereof.

In a further embodiment of the present invention, the transformant may be a transformant plant. The transformant plant according to this embodiment may be obtained by introducing a recombinant vector comprising the polynucleotide of the present invention into a plant to express a polypeptide encoded by the polynucleotide.

Where a recombinant expression vector is used, the recombinant expression vector used to transform the plant is not particularly limited as far as the vector is capable of expressing the polynucleotide of the present invention in said plant. Examples of such vectors include a vector bearing a promoter capable of constitutively expressing the polynucleotide in plant cells, and a vector bearing a promoter inducibly activated by external stimulation.

Examples of the promoter constitutively expressing the polynucleotide in plant cells include 35S RNA promoter of cauliflower mosaic virus, rd29A gene promoter, rbcS promoter, mac-1 promoter, etc.

Examples of the promoter inducibly activated by external stimulation include mouse mammary tumor virus (MMTV) promoter, tetracycline-responsive promoter, metallothioinene promoter, heat shock protein promoter, etc.

Plants that are subject to transformation in the present invention are intended to mean entire plant bodies, plant organs (e.g., leaves, petals, stems, roots, seeds, etc.), plant tissues (e.g., epidermis, phloem, parenchyma, xylem, vascular bundles, palisade tissues, spongy tissues, etc.) or plant culture cells, or may be any of various types of plant cells (e.g., suspension culture cells), protoplasts, leaf slices, calli, and the like. Plant species which are used for transformation are not particularly limited and may be any plant from those belonging to the Monocotyledoneae or the Dicotyledoneae.

Conventional transformation methods (e.g., the *Agrobacterium* method, gene gun method, PEG method, electroporation method, etc.) known to those ordinarily skilled in the art are used for gene transfer to plants. For example, the *Agrobacterium*-mediated method and the method of directly introducing into plant cells are well known. When the *Agrobacterium* method is used, the plant expression vector constructed is introduced into an appropriate *Agrobacterium* strain (e.g., *Agrobacterium tumefaciens*) and this strain is infected to aseptically cultured leaf discs according to the leaf disc method (Hirobumi Uchimiya, Manuals for Plant Gene Manipulation (1990), pp. 27-31, Kodansha Scientific Co., Ltd., Tokyo), etc. to give transgenic plants. The method by Nagel, et al. (Micribiol. Lett., 67: 325 (1990)) may also be used. This method involves introducing first, e.g., an expression vector into *Agrobacterium* and then introducing the transformed *Agrobacterium* into plant cells or plant tissues by the method described in Plant Molecular Biology Manual (Gelvin, S. B. et al., Academic Press Publishers). Herein, the "plant tissue" includes calli obtained by culturing plant cells. When the transformation is carried out using the *Agrobacterium* method, binary vectors (pBI121 or pPZP202, etc.) may be used.

For direct transfer of genes to plant cells or plant tissues, the electroporation method and the particle gun method are known. When a particle gun is used, plant bodies, plant organs or plant tissues per se may be used, or slices may be prepared and then provided for use, or protoplasts may also be prepared and then provided for use. The samples thus prepared can be bombarded using a gene transfer apparatus (e.g., PDS-1000 (BIO-RAD, Inc.), etc.). Bombardment conditions may vary depending upon plants or samples. Normally, the bombardment is performed under a pressure of about 450 to 2000 psi at a distance of about 4 to 12 cm.

The cells or plant tissues into which the gene is introduced are first selected for their chemical resistance such as hygromycin resistance, etc. and then regenerated into plant bodies in a conventional manner. Regeneration of plant bodies from the transformants can be performed by methods known to those skilled in the art, depending upon species of plant cells.

Where a plant culture cell is used as a host, transformation is preformed by introducing the recombinant vector into culture cells by the gene gun method, the electroporation method, etc. Calluses, shoots, hairy roots, etc. resulted from the transformation can be used directly in cell culture, tissue culture or organ culture. Furthermore, they can be regenerated into plant bodies by conventional plant tissue culture methods through administration of plant hormones (e.g., auxin, cytokinin, gibberellin, abscisic acid, ethylene, brassinolide, etc.) at appropriate concentrations.

Whether or not the polynucleotide of the present invention has been introduced into the plant can be confirmed by PCR, Southern hybridization, northern hybridization or the like. For example, DNA is prepared from the transgenic plant and then DNA-specific primers are designed to perform PCR. PCR can be performed under the same conditions as used for the preparation of plasmids described above. Subsequently, the amplified product is subjected to agarose gel electrophoresis, polyacrylamide gel electrophoresis, capillary electrophoresis, etc. and stained with ethidium bromide, SYBR Green solution, etc. By detecting the amplified product as a single band, it can be confirmed that the host has been transformed. Alternatively, PCR may be performed using primers previously labeled with a fluorescent dye or the like, and the amplified product can be detected. Furthermore, there may be employed a method which involves binding the amplified product to a solid phase such as a microplate, etc. and then confirming the product by fluorescence or enzyme reactions.

Once the transgenic plant wherein the polynucleotide of the present invention has been incorporated into the genome is acquired, its progeny can be obtained by sexual or asexual reproduction of the plant body. Furthermore, the plant body can be mass-produced by acquiring from the plant body or its progeny or clones thereof, e.g., seeds, fruits, cut panicles, tubers, tuberous roots, strains, calli, protoplasts, etc., and then using them as the origin. Accordingly, the present invention also encompasses the plant body in which the polynucleotide in accordance with the present invention is expressibly introduced, or progenies of the plant body having the same property as in the plant body, and tissues derived therefrom.

The transformation methods for various plants are already reported. Examples of the transgenic plants in accordance with the present invention include, but not be limited to, solanaceous plants (e.g., eggplant, tomato, green pepper, potato, tobacco, *datura* or downy thorn apple, alkakengi, *petunia, Calibrachoa* sp., *nierembergia*, etc.), leguminous plants (e.g., soybean, azuki bean, peanut, common bean or *Phaseolus vulgaris*, broad bean, Lotus *japonicus*, etc.), rosaceous plants (e.g., strawberry, plum, cherry, rose, blueberry, blackberry, bilberry, cassis, raspberry, *Rubus suauissimus*, etc.), caryophyllaceous plants (carnation, soap root, etc.), *chrysanthemum* plants (*chrysanthemum, gerbera*, sunflower, daisy, *stevia*, etc.), orchidaceous plants (orchid, etc.), primulaceous plants (cyclamen, etc.), gentianaceous plants (lisianthus, gentian, etc.), iridaceous plants (freesia, iris, *gladiolus*, etc.), scrophulariaceous plants (*antirrhinum*, torenia, etc.), *Kalanchoe pinnata* (*Kalanchoe*), liliaceous plants (lily, tulip, etc.), convolvulaceous plants (morning glory, cairo morning glory, moonflower, sweet potato, *Ipomoea quamoclit*, Evolvulus or American blue, etc.), *hydrangea* plants (*hydrangea*, deutzia, etc.), cucurbitaceous plants (bottle gourd, etc.), geraniaceous plants (*pelargonium*, geranium, etc.), oleaceous plants (forsythia, etc.), vitaceous plants (e.g., grapevine, etc.), theaceous plants (*camellia*, tea, etc.), poaceous plants (e.g., rice plant, barley, wheat, oat, rye, sweet corn, foxtail millet, Japanese millet, kaoliang, sugar cane, bamboo, oat, finger millet, sorghum, Indian rice, Job's tears, pasture grass, etc.), moraceous plants (mulberry, hopvine, kouzo or paper mulberry, rubber tree, *Cannabis*, etc.), rubiaceous plants (Arabian coffee, *gardenia*, etc.), fagaceous plants (oak, Buna or Japanese beech, Kashiwa oak, etc.), Pedaliaceae plants (sesame, etc.), rutaceous plants (e.g., daidai orange, yuzu lemon, unshu citrus, Japanese prickly ash), brassicaceous plants (red cabbage, flowering cabbage, Japanese radish, *Arabidopsis*, rapeseed, cabbage, broccoli, cauliflower, etc.), and Lamiaceae plants (*salvia*, Japanese basil, lavender, skull cap, etc.). Particularly preferred examples of the plant for transformation include plants that are known to biosynthesize various glycosides using steviol as the aglycon. Such plants include *stevia*, *Rubus suauissimus*, and the like.

The plant transformed by the polynucleotide of the present invention (hereinafter "the plant of the present invention" or "the plant body of the present invention") can produce steviol glycosides in a higher quantity, as compared with its wild type, so long as it has an appropriate substrate or when an appropriate substrate is externally added.

The plant of the present invention can easily provide a complete plant by cultivating the seeds, cuttings, bulbs, etc. from the plant of the present invention.

Consequently, the plant of the present invention includes entire plant bodies, plant organs (e.g., leaves, petals, stems, roots, seeds, bulbs, etc.), plant tissues (e.g., epidermis, phloem, parenchyma, xylem, vascular bundles, palisade tissues, spongy tissues, etc.) or plant culture cells, or various types of plant cells (e.g., suspension culture cells), protoplasts, leaf slices, calli, and the like.

4. Extract of the Transformant and Use Thereof

In a still further embodiment, the present invention provides an extract of the transformant described above. When it has an appropriate substrate or when an appropriate substrate is externally added, the transformant of the present invention is expected to have a high content of steviol glycosides in its extract, as compared with its wild type.

The transformant of the present invention can be obtained by disrupting the transformant using glass beads, a homogenizer, a sonicator, etc., centrifuging the disrupted product and then recovering the supernatant. An additional step of extraction may also be performed by the procedures for extracting steviol glycosides described above.

The extract of the transformant of the present invention can be used to produce, e.g., food products, pharmaceuticals, industrial materials, and the like.

In a yet further embodiment, the present invention provides foods, pharmaceuticals and industrial materials (raw materials for food, etc.) containing the extract of the transformant of the present invention. The foods, pharmaceuticals and industrial materials containing the extract of the transformant of the present invention may be prepared in a conventional manner. As such, the food products, pharmaceuticals, industrial materials, etc., containing the extract of the transformant of the present invention contains the steviol glycoside produced using the transformant of the present invention.

The food of the present invention includes, for example, a dietary supplement, health food, functional food, food product for young children, geriatric food, etc. As used herein, the food or food product is intended to mean a solid, fluid and liquid food as well as a mixture thereof, and collectively means an edible stuff.

The term dietary supplement refers to food products enriched with specific nutritional ingredients. The term health food refers to food products that are healthful or good for health, and encompasses dietary supplements, natural foods, diet foods, etc. The term functional food refers to a food product for replenishing nutritional ingredients which assist body control functions. Functional foods are synonymous with foods for specified health use. The term food for young children refers to a food product given to children up to about 6 years old. The term geriatric food refers to a food product treated to facilitate digestion and absorption when compared to untreated foods.

In the food product of the present invention, the non-caloric steviol glycoside is used as a sweetener. Accordingly, the food product of the present invention is low calorie and have the advantage that contributes to health promotion or health maintenance.

The shape of these food products may include, for example, bread, noodles, pasta, rice, confectionery (cake, ice cream, ice candy, doughnut, baked cookie, candy, chewing gum, gummy candy and tablet, as well as Japanese confectionery such as rice dumpling, bean paste cake, etc.), agricultural foods such as tofu (soybean curd) and its processed products, etc., fermented foods such as Japanese sake (rice wine), medicinal liquor, mirin (sweet cooking sherry), vinegar, soy sauce, miso (bean paste), etc., livestock food products such as yoghurt, ham, bacon, sausage, etc.; seafood products such as kamaboko (minced and steamed fish), ageten (deep-fried fish cake), hanpen (puffy fish cake), etc., as well as fruit drinks, soft drinks, sports drinks, alcoholic beverages, tea, condiments. The shape of the food products may also include, for example, low-calorie beverage, non-sugar beverage, fruit can, milk beverage, powder beverage, yoghurt, jelly, dressing, men-tsuyu (soy sauce-based seasoning liquid for noodle), Japanese pickle, tsukudani (sea foods boiled in soy sauce), soy sauce, miso (bean paste), shiokara (salted fish guts), Vermont vinegar, pickled shallots in sugared vinegar, sweet pickled ginger, lotus roots pickled in vinegar, Japanese pickles, soy-based sweet sauce for tempura and broiled kabayaki eel, grilled meat sauce, sauce, etc., gum, candy and lollipop, toothpaste, satsuma-age (fried fish cake), dashi-maki (rolled omelet), sauce for pan-fried noodle, sauce for cold noodles, shimesaba (vinegared mackerel fillet), ices, sherbet, soft cream, fish jelly products, refreshments, rice cake, cone cup, seasoned laver, tenkasu (crunchy bits of tempura), furikake (rice seasoning), etc.

Dosage form of the pharmaceutical (composition) of the present invention is not particularly limited and may be any dosage form including the state of a solution, paste, gel, solid or powder. Also, the pharmaceutical composition of the present invention may be used as topical agents for the skin, including an oil, lotion, cream, emulsion, gel, shampoo, hair rinse, hair conditioner, enamel, foundation, lipstick, face powder, facial pack, ointment, powder, tooth paste, aerosol, cleansing foam, etc., bath agent, medicated tonic, skin beauty essence, sun protectant, etc.

The pharmaceutical composition of the present invention may further contain other pharmaceutically active components (e.g., antiinflammatory components) or aid components (e.g., lubricant or carrier components).

5. Method for Screening a Plant with a High Content of Steviol Glycosides

The present invention provides a method for screening a plant with a high content of steviol glycosides. Specifically, the method above comprises steps (1) to (3) below:

(1) a step of extracting mRNA from a test plant;

(2) a step of hybridizing said mRNA or cDNA prepared from said mRNA to a polynucleotide that hybridizes under highly stringent conditions with a polynucleotide consisting of a nucleotide sequence complementary to the polynucleotide of the present invention; and, (3) a step of detecting said hybridization.

The step (1) described above may be performed by extracting mRNA from a test plant. The site of the test plant, from which mRNA is to be extracted, is not particularly limited and preferably, petals. When mRNA is extracted, cDNA may be prepared from mRNA by reverse transcription.

The step (2) can be performed by hybridizing the extracted mRNA above under highly stringent conditions using as a probe or primer a polynucleotide or oligonucleotide consisting of a nucleotide sequence complementary to the polynucleotide of the present invention. The highly stringent conditions are as described above. The polynucleotide or oligonucleotide has a length of preferably 5 to 500 bp, more preferably, 10 to 200 bp, and most preferably, 10 to 100 bp. The polynucleotide or oligonucleotide may be easily synthesized using various automated synthesizer (e.g., AKTA oligopilot plus 10/100 (GE Healthcare)). Alternatively, the synthesis may also be entrusted to a third-party organization (e.g., Promega Inc., or Takara Co.), etc.

Where the polynucleotide consisting of the nucleotide sequence complementary to the polynucleotide of the present invention is used as a probe in the step (2), the step (3) can be performed by ordinary methods for detecting hybridization, including Southern blotting, northern blotting (Sambrook, Fritsch and Maniatis, "Molecular Cloning: A Laboratory Manual" 2nd Edition (1989), Cold Spring Harbor Laboratory Press), Microarray (Affymetrix Inc.; cf, U.S. Pat. Nos. 6,045,996, 5,925,525 and 5,858,659), TaqMan PCR (Sambrook, Fritsch and Maniatis, "Molecular Cloning: A Laboratory Manual" 2nd Edition (1989), Cold Spring Harbor Laboratory Press), Fluorescent In Situ Hybridization (FISH) (Sieben V. J. et al., (2007-06). IET Nanobiotechnology 1 (3): 27-35), etc. On the other hand, where the polynucleotide consisting of the nucleotide sequence complementary to the polynucleotide of the present invention is used as a primer in the step (2), the hybridization can be detected in the step 3 by performing PCR amplification and analyzing the resulting amplification product through electrophoresis or sequencing (Sambrook, Fritsch and Maniatis, "Molecular Cloning: A Laboratory Manual" 2nd Edition (1989), Cold Spring Harbor Laboratory Press), etc.

The plant body where hybridization is detected at a higher level is considered to express the protein having the activity of adding the sugar molecule to the glucose at position 13 of the compound represented by general formula (I) more abundantly compared to other plant bodies, and thus expected to have a higher content of the steviol glycoside.

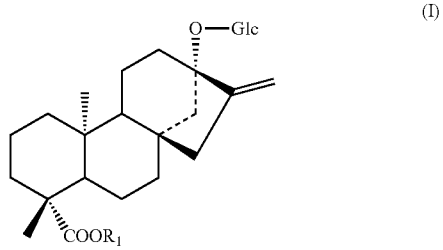

(I)

EXAMPLES

Hereinafter, the present invention will be described more specifically with reference to EXAMPLES below but is not deemed to be limited thereto.

[Example 1] Isolation of Candidate Gene for Steviolbioside Glucosyltransferase

Molecular biological techniques used in this EXAMPLE were performed in accordance with the methods described in Molecular Cloning (Sambrook et al., Cold Spring Harbour Laboratory Press, 2001), unless otherwise specified in detail.

Based on the sequence of the gene for glucosyltransferase found in *stevia* leaves, gene search was performed by PCR. To obtain genes highly homologous to UGT91D1 (GEN-BANK Accession No. AY345980), which was reported to have no activity for steviolmonoside in the prior art (Non-Patent Document 2), PCR was performed with cDNA from *stevia* leaves using the following primer set (SEQ ID NOS: 3 and 4).

The cDNA from *stevia* leaves was obtained by extracting total RNA from *stevia* leaves using an RNeasy Plant Mini Kit (QIAGEN) and subjecting 0.5 μg of the total RNA to reverse transcription (RT) with Random Oligo-dT primer.

```
CACC-NdeI-SrUGT91D1-Fw (the underlined por-
tion
is the NdeI recognition site):
                                    (SEQ ID NO: 3)
5'-CACCCATATGTACAACGTTACTTATCATCA-3'

BamHI-SrUGT91D1-Rv2 (the underlined portion
is the BamHI recognition site):
                                    (SEQ ID NO: 4)
5'-GGATCCTTAACTCTCATGATCGATGGCA-3'
```

A PCR solution (50 μl) had the composition of 1 μl of cDNA from *stevia* leaves, 1× ExTaq buffer (TaKaRaBio), 0.2 mM dNTPs, 0.4 pmol each/μl of the primers and 2.5 U ExTaq polymerase. PCR was performed by reacting at 94° C. for 3 minutes, and then amplifying for a total of 30 cycles of the reaction at 94° C. for 1 minute, 50° C. for 1 minute and 72° C. for 2 minutes. The PCR product was electrophoresed on a 0.8% agarose gel, followed by staining with ethidium bromide. As a result, the amplified band was detected at a size of about 1.4 kb, predicted from each template DNA.

This PCR product was subcloned into a pENTR-TOPO Directional Vector (Invitrogen) by the procedure recommended by the manufacturer. Using a DNA Sequencer model 3100 (Applied Biosystems), primer walking was performed with a synthetic oligonucleotide primer to determine the sequence. The results revealed that four genes highly homologous to UGT91D1 were present. These genes had high homology to known UGT91D1 and were found to be novel UGT genes from *stevia* with difference sequences. UGT91D-like3, which is one of them, was a novel UGT gene of *stevia*, showing sequence identity with UGT91D1 at 98% of the DNA level (different in 27 nucleotides) and 95% of the amino acid level (different in 18 residues) (CDS sequence: SEQ ID NO: 1, amino acid sequence: SEQ ID NO: 2).

[Example 2] Construction of Expression Vector

The ORF fragment of about 1.4 kb from UGT91D-like3 was excised using the restriction enzyme sites (the underlined portions of SEQ ID NOS: 3 and 4) of NdeI and BamHI added to the primer, and ligated into the NdeI and BamHI sites of *Escherichia coli* expression vector pET15b (Novagen, Inc.) to give *Escherichia coli* expression vector of this enzyme gene. His tag located upstream the NdeI site of the vector matched with the open reading frame of UGT91D- like3 gene; it was designed to express the chimeric protein of UGT91D-like3 fused to His tag.

[Example 3] Expression and Purification of Recombinant Protein

To clarify the biochemical functions of the enzyme, the enzyme was expressed in *Escherichia coli*. Using the UGT91D-like3 *Escherichia coli* expression plasmid obtained above, *Escherichia coli* BL21 (DE3) was transformed. The resulting transformants were shake-cultured in 4 ml of LB medium (10 g/l tryptone peptone, 5 g/l yeast extract, 1 g/l NaCl) containing 50 µg/ml of ampicillin at 37° C. overnight. When reached the stationary phase, 4 ml of the culture medium was inoculated onto 80 ml of a medium with the same composition, followed by shake culture at 37° C. IPTG was added in a final concentration of 0.5 mM at the point when the cell turbidity (OD600) reached approximately 0.5. Shake culture was continued at 18° C. for 20 hours.

The following procedures were all performed at 4° C. The transformants cultured were collected by centrifugation (5,000×g, 10 mins.), and suspended by adding 1 ml/g cell of Buffer S [20 mM HEPES buffer (pH 7.5), 20 mM imidazole, 14 mM β-mercaptoethanol]. Subsequently, the suspension was ultrasonicated (15 secs.×8) and then centrifuged (15,000×g, 15 mins.). The supernatant obtained was recovered as a crude enzyme solution. The crude enzyme solution was loaded onto His SpinTrap (GE Healthcare), which had been equilibrated with Buffer S, and centrifuged (70×g, 30 secs.). After washing with the buffer, the proteins bound to the column were eluted stepwise with 5 ml each of Buffer S containing 100 mM and 500 mM imidazole. In each of the eluted fractions, the buffer was replaced through a Microcon YM-30 (Amicon) by 20 mM HEPES buffer (pH 7.5) and 14 mM β-mercaptoethanol (magnification of dialysis, ×1000).

Figure 3:
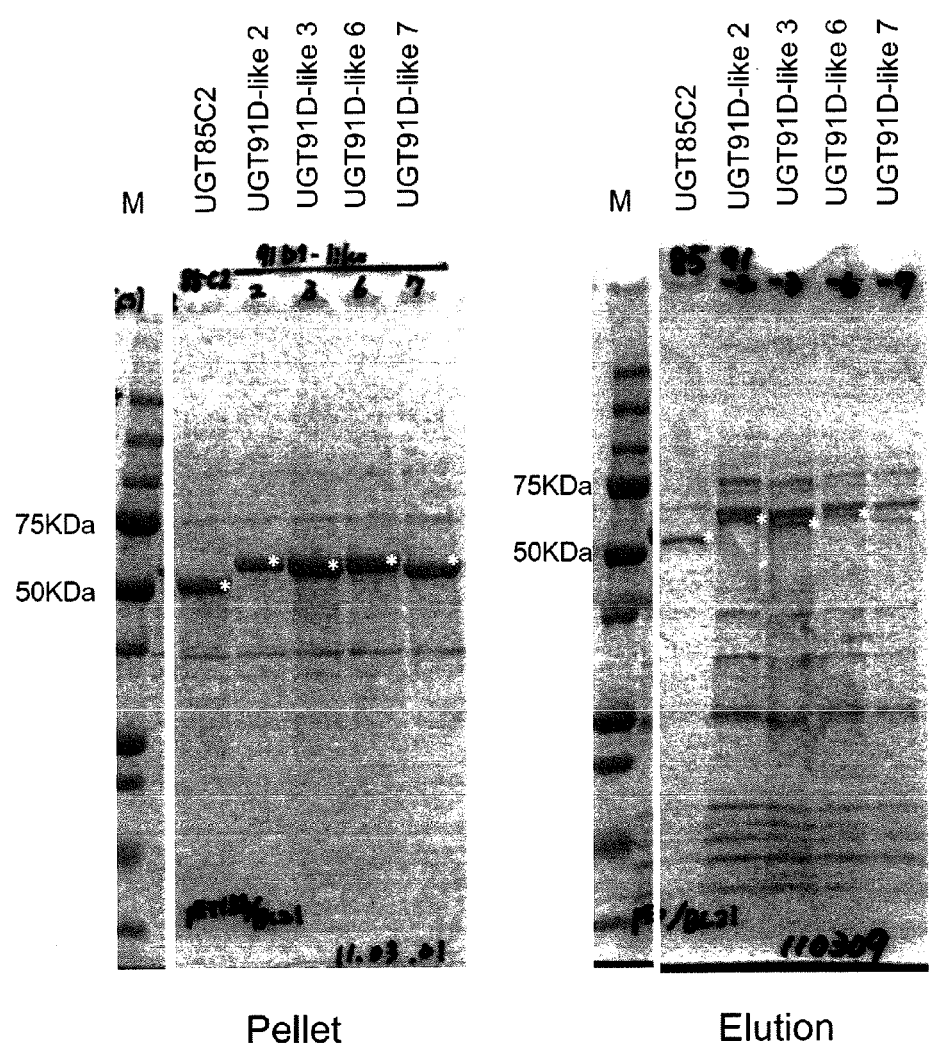
FIG. 3 shows the SDS-PAGE results of *stevia* UGT protein expressed in *Escherichia coli*. The CBB stain patterns with imidazole solution in the pellet fraction are shown in the left side and those in the eluted fraction are shown in the right side. Asterisks denote the expressed recombinant proteins.

As a result of CBB staining after the SDS-PAGE separation, the protein was confirmed in the fraction eluted with 500 mM imidazole at approximately 50 KDa of the estimated molecular weight for the chimeric protein of UGT91D-like3 fused to His tag. Accordingly, this fraction was used for the enzyme analysis (FIG. 3).

[Example 4] Assay for Enzyme Activity of UGT91D-Like3

Standard conditions for the enzyme reaction were as follows: A reaction solution (2 mM UDP-glucose, 0.1 mM glycosyl acceptor substrate, 100 mM potassium phosphate buffer (pH 7.0) and 25 µl of purified UGT91D-like3 enzyme solution) was prepared in distilled water to become 50 µl, and reacted at 30° C. for an hour. LC-MS analysis was performed for 5 µl of the enzyme reaction solution under the following conditions.

LC Conditions
Column: Waters Sunfire C18 3.5 um 2.0 mM I.D.×20 mM
Moving phase: A: MilliQ Water (+0.05% formic acid), B: MeCN
Gradient: linear density gradient from 15% to 55% in B density (20 mins.)
Flow rate: 0.2 ml/min.
Column oven: 40° C.
MS Conditions
ESI (negative mode)
Selected ion monitoring: m/z 317, 479, 641, 687, 803 and 849

Figure 4:
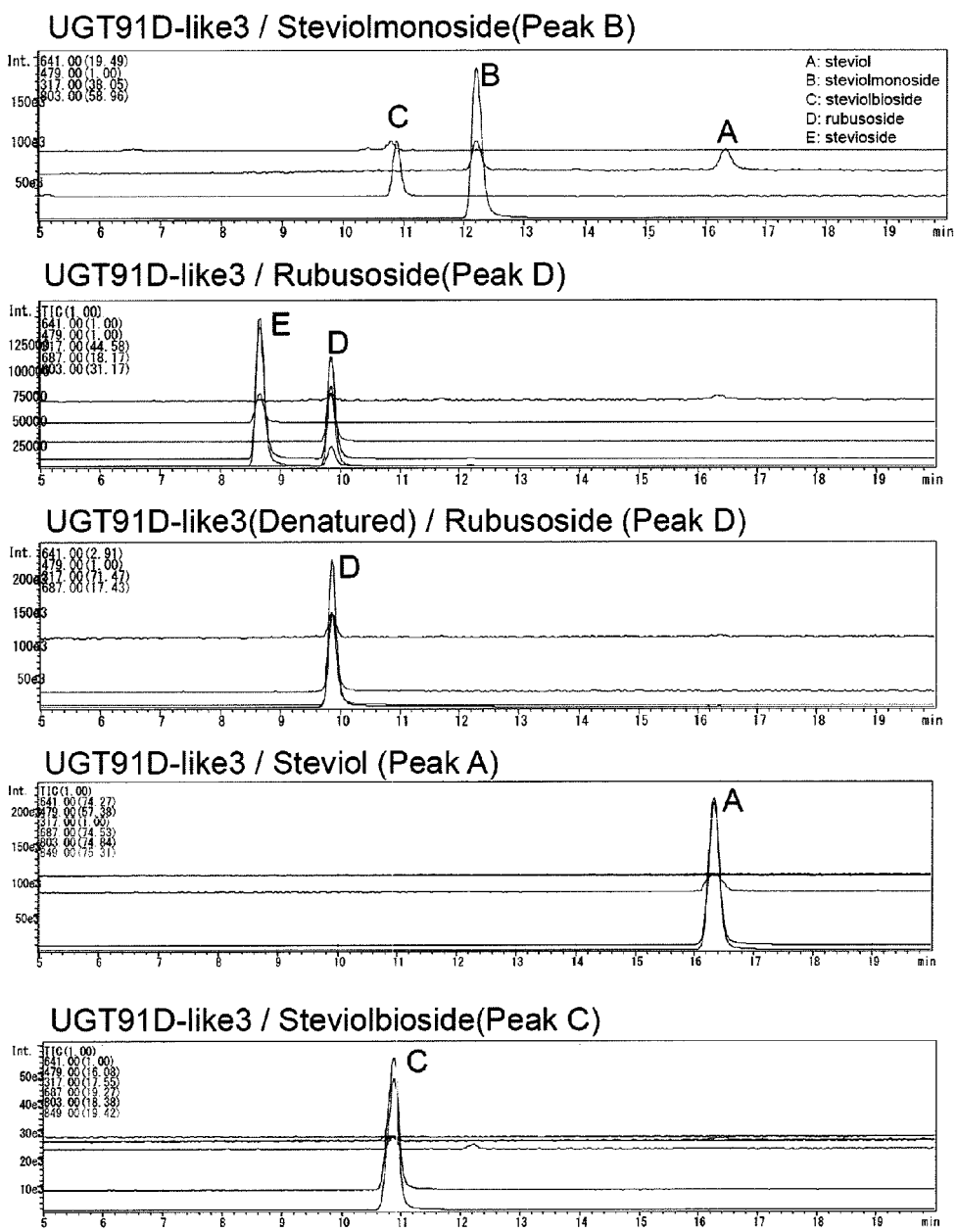
FIG. 4 shows the enzyme activity of UGT91D-like3 protein.

Steviolmonoside (peak B) was prepared by reacting UGT85C2 and steviol (peak A), and the steviolmonoside was reacted with UGT91D-like3. As a result, a new product (peak C) was detected (FIG. 4: panel 1). This peak was identified as steviolbioside based on the retention time and mass fragmentation pattern. Further reaction with rubusoside (peak D) commercially available gave a new peak E, which was identified as stevioside based on the retention time and mass fragmentation pattern (FIG. 4: panel 2). This peak E was confirmed to be the enzyme product since the peak did not appear when UGT91D-like3 inactivated by thermal denaturation (99° C., 3 mins.) was used (FIG. 4: panel 3). Also, steviolmonoside prepared from steviol by the enzyme reaction contained a small quantity of steviol (peak A) (FIG. 4: panel 1), but when steviol (peak A) was reacted with UGT91D-like3, no product was detected (FIG. 4: panel 4). It was confirmed that UGT91D-like3 had the activity of forming steviolbioside (peak C) by glucosylation of steviolmonoside (peak B). When steviolbioside was used as a substrate, any new product was not detected (FIG. 4: panel 5). In addition, known *stevia* includes steviol glycosides conjugated with xylose or rhamnose at the 2-position of 13-glucose in steviol (FIG. 1); UGT91D-like3 did not use UDP-xylose as the sugar donor. The foregoing results revealed that UGT91D-like3 is a novel glucosyltransferase having the activity of specifically catalyzing the glucosylation of position 2 of glucose added at the position 13 of steviol.

[Example 5] Synthesis of Rebaudioside a from Steviol

It became clear that UGT91D-like3 found in *stevia* have the activity of 2-O-glucosylating toward the glucose at the C13-position of steviolmonoside to form steviolbioside and the activity of 2-O-glucosylating toward the glucose at the C13-position of rubusoside to form stevioside. This finding revealed a glucosyltransferase in the biosynthetic pathway to natural sweetener rebaudioside A through glucosylation from steviol four times (FIG. 2).

In order to verify if expression of four of UGT85C2 (CDS sequence: SEQ ID NO: 5, amino acid sequence: SEQ ID NO: 6), UGT91D-like3 (CDS sequence: SEQ ID NO: 1, amino acid sequence: SEQ ID NO: 2), UGT74G1 (CDS sequence: SEQ ID NO: 7, amino acid sequence: SEQ ID NO: 8) and UGT76G1 (CDS sequence: SEQ ID NO: 9, amino acid sequence: SEQ ID NO: 10) is actually necessary and sufficient for biosynthesis of rebaudioside A, it was attempted to express these four glucosyltransferase (UGT) genes in yeast.

Each of the UGT genes was amplified from cDNA of *stevia* leaves by PCR using the following primer set.

```
Primer set for UGT85C2 gene amplification
CACC-NdeI-SrUGT85C2-Fw
(the underlined portion is the NdeI recognition
site):
                                       (SEQ ID NO: 11)
5'-CACCCATATGGATGCAATGGCTACAACTGAGAA-3'

BglII-SrUGT85C2-Rv
(the underlined portion is the BglII recognition
site):
                                       (SEQ ID NO: 12)
5'-AGATCTCTAGTTTCTTGCTAGCACGGTGATTT-3'
```

-continued

Primer set for UGT91D-like3 gene amplification
CACC-NdeI-SrUGT91D1-Fw
(the underlined portion is the NdeI recognition site):
(SEQ ID NO: 3)
5'-CACC<u>CATATG</u>TACAACGTTACTTATCATCA-3'

(SEQ ID NO: 4)
5'-<u>GGATCC</u>TTAACTCTCATGATCGATGGCA-3'

Primer set for UGT74G1 gene amplification
CACC-NdeI-SrUGT74G1-Fw
(the underlined portion is the NdeI recognition site):
(SEQ ID NO: 13)
5'-CACC<u>CATATG</u>GCGGAACAACAAAAGATCAAGAAAT-3'

BamHI-SrUGT74G1-Rv
(the underlined portion is the BamHI recognition site):
(SEQ ID NO: 14)
5'-<u>GGATCC</u>TTAAGCCTTAATTAGCTCACTTACAAATT-3'

Primer set for UGT76G1 gene amplification
CACC-NdeI-SrUGT76G1-Fw
(the underlined portion is the NdeI recognition site):
(SEQ ID NO: 15)
5'-CACC<u>CATATG</u>GAAAATAAAACGGAGACCA-3'

BamHI-SrUGT76G1-Rv
(the underlined portion is the BamHI recognition site):
(SEQ ID NO: 16)
5'-<u>GGATCC</u>TTACAACGATGAAATGTAAGAAACTA-3'

A PCR solution (50 µl) had the composition of 1 µl of cDNA from *stevia* leaves, 1×KOD plus buffer (TOYOBO), 0.2 mM dNTPs, 0.4 pmol each/µl of the primers, 1 mM MgSO4 and 1 U thermostable KOD plus polymerase. PCR was performed by reacting at 95° C. for 5 minutes, and then amplifying for a total of 30 cycles of the reaction at 94° C. for 0.5 minutes, 50° C. for 0.5 minutes and 68° C. for 2 minutes. Each PCR product was subjected to electrophoresis on a 0.8% agarose gel, followed by staining with ethidium bromide. As a result, the amplified band was detected at a size of about 1.4 kb, predicted from each template DNA.

This PCR product was subcloned into a pENTR-TOPO Directional Vector (Invitrogen) by the procedure recommended by the manufacturer. Using a DNA Sequencer model 3100 (Applied Biosystems), primer walking was performed with a synthetic oligonucleotide primer to determine the sequence. It was thus confirmed that the UGT genes, namely, all UGT genes of UGT85C2, UGT91D-like3, UGT74G1 and UGT76G1, were successfully cloned.

The following primer set was designed to incorporate these four UGT genes into yeast expression vector.

SrUGT85C2 Set
Bgl2-UGT85C2-F
(the underlined portion is the BglII recognition site):
(SEQ ID NO: 17)
5'-AC<u>AGATCT</u>ATGGATGCAATGGCTACAACTGAGA-3'

Sal-UGT85C2-R
(the underlined portion is the SalI recognition site):
(SEQ ID NO: 18)
5'-TA<u>GTCGAC</u>TAGTTTCTTGCTAGCACGGTGATTTC-3'

SrUGT91D-like3 Set
NotI-UGT91DIL3-F
(the underlined portion is the NotI recognition site):
(SEQ ID NO: 19)
5'-AA<u>GCGGCCGC</u>ATGTACAACGTTACTTATCATCAAAATTCAAA-3'

Pac-UGT91D1L3-R
(the underlined portion is the PacI recognition site):
(SEQ ID NO: 20)
5'-CG<u>TTAATTAA</u>CTCTCATGATCGATGGCAACC-3'

SrUGT74G1 Set
Not-UGT74G1-F
(the underlined portion is the NotI recognition site):
(SEQ ID NO: 21)
5'-AA<u>GCGGCCGC</u>ATGGCGGAACAACAAAAGATCAAG-3'

Pac-UGT74G1-R
(the underlined portion is the PacI recognition site):
(SEQ ID NO: 22)
5'-CG<u>TTAATTAA</u>GCCTTAATTAGCTCACTTACAAATTCG-3'

SrUGT76G1 Set
Bam-UGT76G1-F
(the underlined portion is the BamHI recognition site):
(SEQ ID NO: 23)
5'-AA<u>GGATCC</u>ATGGAAAATAAAACGGAGACCACCG-3'

Sal-UGT76G1-R
(the underlined portion is the SalI recognition site):
(SEQ ID NO: 24)
5'-GC<u>GTCGAC</u>TTACAACGATGAAATGTAAGAAACTAGAGACTCTAA-3'

In the combination of the following primers:
SrUGT85C2 set using UGT85C2 as a template,
SrUGT91D-like3 set using UGT91D-like 3 as a template,
SrUGT74G1 set using UGT74G1 as a template, or,
SrUGT76G1 set using UGT76G1 as a template,
PCR was performed for amplification using a thermostable KOD DNA polymerase (Toyobo) to insert the restriction enzyme site into both ends of each ORF. The DNA fragment obtained was subcloned using a Zero Blunt-TOPO PCR Cloning kit (Invitrogen). The sequence was determined by primer walking with a synthetic oligonucleotide primer using a DNA Sequencer Model 3100 (Applied Biosystems); it was confirmed that the UGT genes of interest were cloned, respectively.

Using a pESC yeast expression system (Stratagene), the following expression vector was constructed to express the four UGT genes described above simultaneously.

(1) Construction of Plasmid pESC-URA-UGT-1

UGT85C2 was excised with restriction enzyme BglII and restriction enzyme SalI, and ligated to the product resulting from cleavage of vector pESC-URA (Stratagene) with restriction enzyme BamHI and restriction enzyme SalI to give plasmid pESC-URA-UGT-1. The product resulting from cleavage of this plasmid pESC-URA-UGT-1 with restriction enzyme NotI and restriction enzyme PacI was ligated to the product from cleavage of UGT91D-like3 with restriction enzyme NotI and restriction enzyme PacI to give pESC-URA-UGT-12.

(2) Construction of Plasmid pESC-HIS-UGT-34

UGT76G1 was excised with restriction enzyme BamHI and restriction enzyme SalI, and ligated to the product resulting from cleavage of vector pESC-HIS (Stratagene) with the same restriction enzymes to give plasmid pESC-HIS-UGT-4. The product resulting from cleavage of this plasmid pESC-HIS-UGT-4 with restriction enzyme NotI and restriction enzyme PacI was ligated to the product from cleavage of UGT74G1 with NotI and PacI to give pESC-HIS-UGT34.

Transformation of Yeast

*Saccharomyces cerevisiae* YPH500 (ura3-52 lys2-801$^{amber}$ ade2-101$^{ochre}$ trp1-Δ63 his3-Δ200 leu2-Δ1α) as a host was transformed with plasmids pESC-URA-UGT-12 and pESC-HIS-UGT-34 by the lithium acetate method. The transformants that grew in SC-Ura&His agar medium (6.7 g of yeast nitrogen base without amino acids, 20 g of glucose, 1.3 g of Amino Acid Mix Powder—Ura&His and 20 g of Bacto agar per 1 L) were selected to name UGT-1234 strain #1, UGT-1234 strain #2. Amino Acid Mix Powder—Ura&His was prepared by blending 2.5 g of adenine sulfate, 1.2 g of L-arginine hydrochloride, 6.0 g of L-aspartic acid, 6.0 g of L-glutamic acid, 3.6 g of L-leucine, 1.8 g of L-lysine, 1.2 g of L-methionine, 3.0 g of L-phenylalanine, 22.5 g of L-serine, 12 g of L-threonine, 2.4 g of L-tryptophane, 1.8 g of L-tyrosine, and 9.0 g of L-valine. On the other hand, transformation was carried out in the same manner as described above using vector pESC-URA and vector pESC-HIS. The resulting transformant was used as the control strain.

Induction and Analysis of Transferase Gene Expression

The transformants UGT-1234 strain #1, UGT-1234 strain #2 and control strain obtained were cultured as follows. First as a pre-culture, each transformant was inoculated into 10 ml of SC-Ura&His liquid medium (SC-Ura&His agar medium without Bacto agar), and shake cultured at 30° C. for a day. Next, 1 ml of the pre-culture broth was taken for main culture and inoculated into 10 ml of SG-Ura&His liquid medium (6.7 g of Yeast nitrogen base without amino acids, 20 g of galactose and 1.3 g of Amino Acid Mix Powder—Ura&His per 1 L), followed by shake culture at 30° C. for a day.

In order to confirm if expression of the four UGT genes was induced, the cells were collected from the culture broth and total RNA was purified using a RNeasy Mini Kit.

The total RNA (1 μg) was taken and used to synthesize cDNA by Super Script II reverse transcriptase (Invitrogen), using a random hexamer as a primer.

In order to confirm expression of the four UGT genes, the following primers were prepared.

```
For confirmation of UGT85C2 expression
UGT85C2-r1:
                                       (SEQ ID NO: 25)
5'-CAAGTCCCCAACCAAATTCCGT-3'

For confirmation of UGT91D-like3 expression
UGT91D1L3-r1:
                                       (SEQ ID NO: 26)
5'-CACGAACCCGTCTGGCAACTC-3'

For confirmation of UGT74G1 expression
UGT74G1-r1:
                                       (SEQ ID NO: 27)
5'-CCCGTGTGATTTCTTCCACTTGTTC-3'

For confirmation of UGT76G1 expression
UGT76G1-r1:
                                       (SEQ ID NO: 28)
5'-CAAGAACCCATCTGGCAACGG-3'

GAL10p region (promoter region)
PGAL10-f3:
                                       (SEQ ID NO: 29)
5'-GATTATTAAACTTCTTTGCGTCCATCCA-3'
```

```
-continued
GAL1p region (promoter region)
PGAL1-f3:
                                       (SEQ ID NO: 30)
5'-CCTCTATACTTTAACGTCAAGGAGAAAAAACC-3'
```

It was confirmed by PCR with the combination of primers of the following SEQ ID NOS, using the previously synthesized cDNA as a template using an ExTaq (Takara Bio) that each UGT gene was expressed:

```
UGT85C2:
                                       (SEQ ID NO: 25)
UGT85C2-r1
and
                                       (SEQ ID NO: 30)
PGAL1-f3;

UGT91D-like3:
                                       (SEQ ID NO: 26)
UGT91D1L3-r1
and
                                       (SEQ ID NO: 29)
PGAL10-f3;

UGT74G1:
                                       (SEQ ID NO: 27)
UGT74G1-r1
and
                                       (SEQ ID NO: 30)
PGAL1-f3;

UGT76G1:
                                       (SEQ ID NO: 28)
UGT76G1-r1
and
                                       (SEQ ID NO: 29)
PGAL10-f3.
```

The PCR products of expected sizes were obtained, respectively, in UGT-1234 strain #1 and UGT-1234 strain #2, whereas in the control strain, no PCR product was obtained. It was confirmed by this that the four UGT genes introduced were all expressed in UGT-1234 strain #1, UGT-1234 strain #2.

Production of Steviol Glycoside

Culture was performed under the same conditions as in "Induction and analysis of transferase gene expression" described above, except that 0.5 μg of steviol (ChromaDex Inc.) was added per 1 ml of the medium for main culture. After completion of the culture, the culture broth was centrifuged to separate the supernatant and the cells. The cells were suspended in water, disrupted with glass beads and then centrifuged to recover the supernatant. The cell-disrupted supernatant and the culture supernatant were washed with acetonitrile, respectively, and then passed through a Sep-Pak C18 column, which had been equilibrated with water. After washing with 20% acetonitrile, elution was performed with 50% acetonitrile. After drying to harden, the product was dissolved in a small quantity of acetonitrile to prepare a glycoside sample. This glycoside sample was provided for subsequent analysis.

Confirmation of the Products by Thin Layer Chromatography (TLC)

The glycoside samples described above were applied to a silica gel plate for TLC (Merck) and developed using chloroform:methanol:water=65:35:10 (lower layer) as a developing solvent. After development, 5% sulfuric acid was sprayed, followed by heating on a plate at 120° C. for 5 to 10 minutes. As a result, spots considered to be steviolmonoside, steviolbioside, rubusoside, stevioside and rebaudioside A were confirmed in the supernatant samples of UGT-1234 strain #1 and UGT-1234 strain #2. On the other hand, any spot considered to be the glycoside of any steviol was not confirmed in the cell-disrupted supernatant samples of UGT-1234 strain #1 and UGT-1234 strain #2, the cell-disrupted supernatant sample of the control strain and the culture supernatant sample.

Confirmation of the Products by LC-MS

Next, the glycoside samples described above were subjected to LC-MS analysis under the following conditions for analysis.

LC Conditions

Column: CAPCELL PAK C18 (5 μm, 2.0 mM I.D.×150 mM)

Moving phase: A: MilliQ Water (+0.05% formic acid), B: acetonitrile 15%-67% B/(A+B) for 26 mins.

Flow rate: 0.2 ml/min.

Column temperature: 40° C.

Volume injected: 5 μl

MS Conditions

Analysis mode: selected ion monitoring (negative)

Selected ion monitoring: m/z 849, 803, 687, 641, 479, 317, 965

Figure 5:
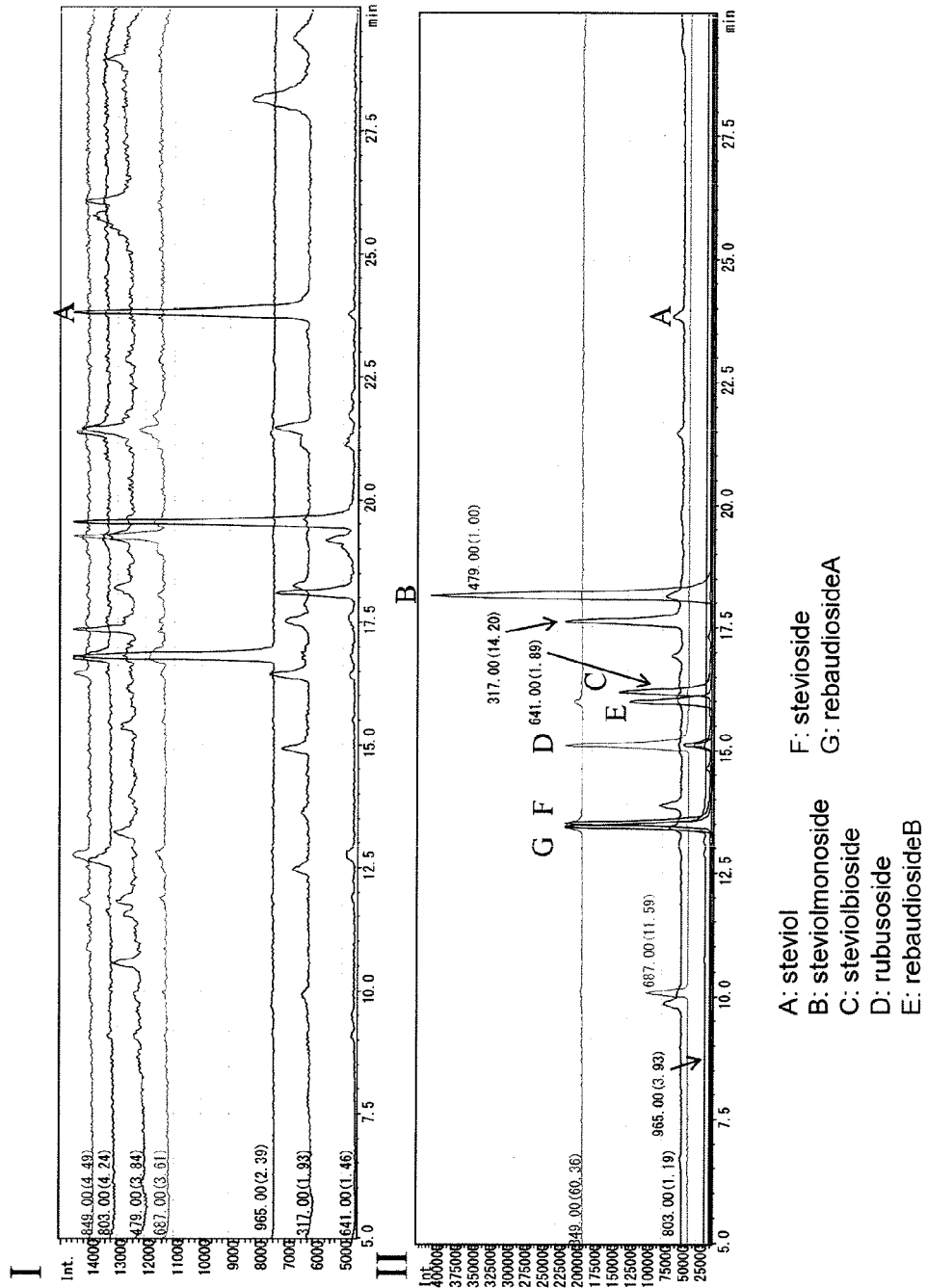
FIG. 5 shows the results of LC-MS analysis of the culture broth of recombinant yeast into which UGT85C2, UGT91D-like3, UGT74G1 and UGT76G1 genes were introduced.

As a result of the analysis, steviol glycosides were detected specifically in independent two strains of the transformed yeast (FIG. 5II: UGT-1234 strain #1: peak A shows steviol added as a substrate). It was revealed that these glycosides were steviolmonoside (FIG. 5 II: peak B), steviolbioside (FIG. 5 II: peak C), rubusoside (FIG. 5: peak D), rebaudioside B (FIG. 5 II: peak E), stevioside (FIG. 5 II: peak F) and A rebaudioside A (FIG. 5 II: peak G) from their retention times and MS values. A strain into which the vector alone was introduced (negative control) was subjected to the same analysis but these glycosides were not substantially detected (FIG. 5I).

It is thus considered that the glycosides would be secreted into the medium after synthesis in the cells.

The results of EXAMPLES 4 and 5 indicate that rebaudioside A can be produced in yeast from steviol by the four UGT enzymes.

[Example 6] Comparison in Activity Between Recombinant Proteins

Expression of UGT91D2e Protein

The enzyme activities were compared and evaluated between UGT91D-like3 of the invention and UGT91D2e (CDS sequence: SEQ ID NO: 31, amino acid sequence: SEQ ID NO: 32) described in the prior art publication (Patent Document 3).

As given below, the *Escherichia coli* expression construct of UGT91D2e was prepared, and the enzyme activities of UGT91D2e and UGT91D-like3 were evaluated by the same manner as in EXAMPLES 3 and 4.

Upon cloning of UGT91D2e, amplification by PCR was performed with specific primers of SEQ ID NO: 33 and SEQ ID NO: 34, using the above UGT91D-like3 as a template. The UGT91D2e fragment amplified was inserted into a pET15b expression vector using a GeneArt Seamless System (Life Technologies Corp.) by the method recommended by the manufacturer. After confirming the correct nucleotide sequence of the inserted fragment by sequencing, the *Escherichia coli* BL21 (DE3) strain (Life Technologies Corp.) was transformed with this expression plasmid to express UGT91D2e as a HisTag fusion protein.

SrUGT91D1-3-Art-<u>NdeI</u>-FW
(the underlined is the NdeI recognition site):
(SEQ ID NO: 33)
5'-GTGCCGCGCGGCAGC<u>CATATG</u>GCTACCAGTGACTCCATAG-3'

SrUGT91D1-3-Art-<u>BamHI</u>-RV
(the underlined is the BamHI recognition site):
5'-CTTTGTTAGCAGCC<u>GGATCC</u>TTAACTCTCATGATCGATGGCAAC-3'
(SEQ ID NO: 34)

Detection of the Expression Proteins by Western Blotting

The HisTag fusion UGT91D2e protein and the HisTag fusion UGT91D-like3 protein described above were purified in the same manner as in EXAMPLE 3 by passing the supernatant fraction of *Escherichia coli* cell lysate through the HisSpinTrap column. The purified protein fraction eluted with 500 mM imidazole was subjected to electrophoresis in acrylamide gel Multi-MiniGel II (10/20) (Cosmo Bio Co.) (30V, 60 mins.). The protein on the electrophoresis gel was blotted to an Immobilon-P Membrane (Millipore Corp.) according onto the procedure described below.

The electrophoresis gel was equilibrated with a blotting buffer (5.82 g of Tris, 2.93 g of glycine, 200 ml of methanol and 1 ml of 10% (v/v) SDS were diluted with water to make 1 L) for 20 minutes, and then blotted to a membrane, which had been previously immersed in the blotting buffer using a blotting machine Trans-Blot SD Semi-Dry Transfer Cell (BioRad Inc.), at 15V over 30 minutes.

After blotting, the membrane was gently washed with TBS-T buffer (TBS Buffer: to 500 ml of 1M Tris-HCl was added 87.5 g of NaCl, the mixture was diluted with and dissolved in water to make 1 L, and 0.1% (v/v) Tween 20 was then added to the solution), followed by blocking with TBS-T buffer containing 1% (w/v) skimmed milk for an hour. Subsequently, the membrane was washed gently with TBS-T buffer.

The anti-His monoclonal antibody/mouse (Novagen, Inc.) was diluted with TBS-T buffer to 1000-fold. The dilution was applied onto the protein-blotted surface to spread over the entire membrane surface and incubated at room temperature for an hour (primary antibody treatment). Thereafter, the membrane was gently rinsed with TBS-T buffer, and then washed three times with TBS-T buffer for 5 minutes each.

Next, the anti-mouse IgG antibody (horse radish peroxidase-linked) (GE Healthcare) was diluted with TBS-T buffer to 50000-fold, and the primary antibody-treated membrane was soaked in the dilution, followed by gentle shaking at room temperature for an hour (secondary antibody treatment). Then, the membrane was gently rinsed with TBS-T buffer. Washing with TBS-T buffer for 5 minutes was repeated 3 times.

Detection was performed according to the procedure recommended by the manufacturer using an Amersham ECL-Prime Western Blotting Detection Reagents Kit (GE Healthcare). The blotting surface was treated with detection reagents and incubated at room temperature for 5 minutes to detect the expression protein with a ChemiDoc XRS+ System (BioRad Inc.) (FIG. 6). No band was detected in the pET15 vector control, but in UGT91D-like3, a band was detected at a slightly larger size than 50 kDa, as predicted from the amino acid sequence. Similarly, a band was detected in UGT91D2e at a slightly smaller size than in UGT91D-like3, which was confirmed to be expressed as the 12 amino acid-short protein. The partial sequences of UGT91D1, UGT91D-like3 and UGT91D2e at the N-terminal sites are shown in FIG. 7.

Comparison in Relative Enzyme Activity

The enzyme activities were compared between the purified proteins of UGT91D-like3 and UGT91D2e expressed in *Escherichia coli*. Using rubusoside as substrate, the comparison was made under the same enzyme reaction conditions and analysis conditions as in EXAMPLE 4. A relative enzyme activity was calculated by dividing the amount of stevioside produced by the amount of the protein provided for the reaction. As a result, UGT91D-like3 showed 167% when the glucosylation activity of UGT91D2e was made 100%. The results indicate that the relative enzyme activity of UGT91D-like3 per protein amount was higher by 67% than UGT91D2e.

Considering that the full length UGT91D-like3 protein is 485 amino acid residues, it is an extremely remarkable effect that the activity was increased even by 67% due to the presence of only 12 residues (percentage of the total residues: (12/485)×100=3.09%).

Results

As is clear from the sequence comparison with other glucosyltransferases including UGT91D1, UGT91D-like3 is considered as a full-length glucosyltransferase involved in glucosylations of steviol glycosides. In addition, it was experimentally demonstrated that UGT91D-like3 possesses a relative enzyme activity with 67% higher than UGT91D2e due to the presence of N-terminal 12 amino acids.

INDUSTRIAL APPLICABILITY

According to the present invention, the C2-hydroxy group of the glucose at the C13-position of steviolmonoside and rubusoside can be glycosylated using the UGT91D-like3 gene and the sweetness and quality of taste steviol glycosides can be improved. The present invention has clarified the whole picture of the biosynthetic pathway up to rebaudioside A, and provides a molecular tool for producing non-caloric natural sweeteners rebaudioside A, stevioside and other analogous compounds not only in plants but also in microorganisms.

SEQUENCE LISTING FREE TEXT

SEQ ID NO: 3: synthetic DNA
SEQ ID NO: 4: synthetic DNA
SEQ ID NO: 11: synthetic DNA
SEQ ID NO: 12: synthetic DNA
SEQ ID NO: 13: synthetic DNA
SEQ ID NO: 14: synthetic DNA
SEQ ID NO: 15: synthetic DNA
SEQ ID NO: 16: synthetic DNA
SEQ ID NO: 17: synthetic DNA
SEQ ID NO: 18: synthetic DNA
SEQ ID NO: 19: synthetic DNA
SEQ ID NO: 20: synthetic DNA
SEQ ID NO: 21: synthetic DNA
SEQ ID NO: 22: synthetic DNA
SEQ ID NO: 23: synthetic DNA
SEQ ID NO: 24: synthetic DNA
SEQ ID NO: 25: synthetic DNA
SEQ ID NO: 26: synthetic DNA
SEQ ID NO: 27: synthetic DNA
SEQ ID NO: 28: synthetic DNA
SEQ ID NO: 29: synthetic DNA
SEQ ID NO: 30: synthetic DNA
SEQ ID NO: 33: synthetic DNA
SEQ ID NO: 34: synthetic DNA

The invention claimed is:

1. An expression vector comprising a heterologous expression control region and a polynucleotide according to any one selected from (a) to (d) below:
   (a) a polynucleotide comprising the nucleotide sequence of SEQ ID NO: 1;
   (b) a polynucleotide encoding a protein consisting of the amino acid sequence of SEQ ID NO: 2;
   (c) a polynucleotide having at least 99% sequence identity with the full length of the nucleotide sequence of SEQ ID NO: 1, and having an activity of adding a sugar molecule to the glucose at position 13 of a compound represented by general formula (I) below; and
   (d) a polynucleotide encoding a protein having an amino acid sequence having at least 99% sequence identity with the full length of the amino acid sequence of SEQ ID NO: 2, and having an activity of adding a sugar molecule to the glucose at position 13 of a compound represented by general formula (I) below:

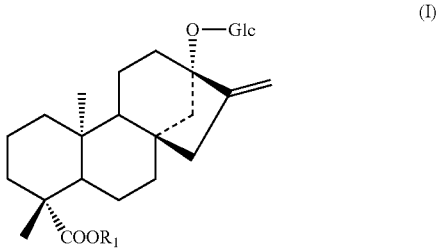

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

2. The expression vector according to claim 1, wherein the sugar molecule is a hexose.

3. The expression vector according to claim 1, wherein the sugar molecule is one selected from glucose, mannose, and galactose.

4. The expression vector according to claim 1, wherein said $R_1$ is H or the sugar residue which is a glucose monomer or a glucose dimer.

5. The expression vector according to claim 1, wherein the compound is steviolmonoside or rubusoside.

6. A non-human transformant, into which the expression vector according to claim 1 is introduced.

7. The transformant according to claim 6, which is a plant.

8. A method for producing a steviol glycoside, which comprises producing the steviol glycoside with the non-human transformant according to claim 6.

9. The method according to claim 8, wherein the steviol glycoside is steviolbioside, stevioside, rebaudioside A, rebaudioside B, rebaudioside C, rebaudioside D, rebaudioside E, rebaudioside F, or a combination thereof.

10. The method according to claim 8, wherein the steviol glycoside is steviolbioside, rebaudioside A, stevioside, or rebaudioside B.

11. The method according to claim 8, wherein the steviol glycoside is steviolbioside or stevioside.

* * * * *

SEQUENCE LISTING

```
<160> NUMBER OF SEQ ID NOS: 36

<210> SEQ ID NO 1
<211> LENGTH: 1458
<212> TYPE: DNA
<213> ORGANISM: Stevia rebaudiana
<220> FEATURE:
<221> NAME/KEY: CDS
<222> LOCATION: (1)..(1455)

<400> SEQUENCE: 1 atg tac aac gtt act tat cat caa aat tca aaa gca atg gct acc agt      48
Met Tyr Asn Val Thr Tyr His Gln Asn Ser Lys Ala Met Ala Thr Ser
1               5                   10                  15 gac tcc ata gtt gac gac cgt aag cag ctt cat gtt gcg acg ttc cca      96
Asp Ser Ile Val Asp Asp Arg Lys Gln Leu His Val Ala Thr Phe Pro
            20                  25                  30 tgg ctt gct ttc ggt cac atc ctc cct tac ctt cag ctt tcg aaa ttg     144
Trp Leu Ala Phe Gly His Ile Leu Pro Tyr Leu Gln Leu Ser Lys Leu
        35                  40                  45 ata gct gaa aag ggt cac aaa gtc tcg ttt ctt tct acc acc aga aac     192
Ile Ala Glu Lys Gly His Lys Val Ser Phe Leu Ser Thr Thr Arg Asn
    50                  55                  60 att caa cgt ctc tct tct cat atc tcg cca ctc ata aat gtt gtt caa     240
Ile Gln Arg Leu Ser Ser His Ile Ser Pro Leu Ile Asn Val Val Gln
65                  70                  75                  80 ctc aca ctt cca cgt gtc caa gag ctg ccg gag gat gca gag gcg acc     288
Leu Thr Leu Pro Arg Val Gln Glu Leu Pro Glu Asp Ala Glu Ala Thr
                85                  90                  95
```

```
act gac gtc cac cct gaa gat att cca tat ctc aag aag gct tct gat    336
Thr Asp Val His Pro Glu Asp Ile Pro Tyr Leu Lys Lys Ala Ser Asp
        100                 105                 110 ggt ctt caa ccg gag gtc acc cgg ttt cta gaa caa cac tct ccg gac    384
Gly Leu Gln Pro Glu Val Thr Arg Phe Leu Glu Gln His Ser Pro Asp
            115                 120                 125 tgg att att tat gat tat act cac tac tgg ttg cca tcc atc gcg gct    432
Trp Ile Ile Tyr Asp Tyr Thr His Tyr Trp Leu Pro Ser Ile Ala Ala
130                 135                 140 agc ctc ggt atc tca cga gcc cac ttc tcc gtc acc act cca tgg gcc    480
Ser Leu Gly Ile Ser Arg Ala His Phe Ser Val Thr Thr Pro Trp Ala
145                 150                 155                 160 att gct tat atg gga ccc tca gct gac gcc atg ata aat ggt tca gat    528
Ile Ala Tyr Met Gly Pro Ser Ala Asp Ala Met Ile Asn Gly Ser Asp
                165                 170                 175 ggt cga acc acg gtt gag gat ctc acg aca ccg ccc aag tgg ttt ccc    576
Gly Arg Thr Thr Val Glu Asp Leu Thr Thr Pro Pro Lys Trp Phe Pro
            180                 185                 190 ttt ccg acc aaa gta tgc tgg cgg aag cat gat ctt gcc cga ctg gtg    624
Phe Pro Thr Lys Val Cys Trp Arg Lys His Asp Leu Ala Arg Leu Val
        195                 200                 205 cct tac aaa gct ccg ggg ata tct gat gga tac cgt atg ggg ctg gtt    672
Pro Tyr Lys Ala Pro Gly Ile Ser Asp Gly Tyr Arg Met Gly Leu Val
    210                 215                 220 ctt aag gga tct gat tgt ttg ctt tcc aaa tgt tac cat gag ttt gga    720
Leu Lys Gly Ser Asp Cys Leu Leu Ser Lys Cys Tyr His Glu Phe Gly
225                 230                 235                 240 act caa tgg cta cct ctt ttg gag aca cta cac caa gta ccg gtg gtt    768
Thr Gln Trp Leu Pro Leu Leu Glu Thr Leu His Gln Val Pro Val Val
                245                 250                 255 ccg gtg gga tta ctg cca ccg gaa ata ccc gga gac gag aaa gat gaa    816
Pro Val Gly Leu Leu Pro Pro Glu Ile Pro Gly Asp Glu Lys Asp Glu
            260                 265                 270 aca tgg gtg tca atc aag aaa tgg ctc gat ggt aaa caa aaa ggc agt    864
Thr Trp Val Ser Ile Lys Lys Trp Leu Asp Gly Lys Gln Lys Gly Ser
        275                 280                 285 gtg gtg tac gtt gca tta gga agc gag gtt ttg gtg agc caa acc gag    912
Val Val Tyr Val Ala Leu Gly Ser Glu Val Leu Val Ser Gln Thr Glu
    290                 295                 300 gtt gtt gag tta gca ttg ggt ctc gag ctt tct ggg ttg cca ttt gtt    960
Val Val Glu Leu Ala Leu Gly Leu Glu Leu Ser Gly Leu Pro Phe Val
305                 310                 315                 320 tgg gct tat aga aaa cca aaa ggt ccc gcg aag tca gac tcg gtg gag    1008
Trp Ala Tyr Arg Lys Pro Lys Gly Pro Ala Lys Ser Asp Ser Val Glu
                325                 330                 335 ttg cca gac ggg ttc gtg gaa cga act cgt gac cgt ggg ttg gtc tgg    1056
Leu Pro Asp Gly Phe Val Glu Arg Thr Arg Asp Arg Gly Leu Val Trp
            340                 345                 350 acg agt tgg gca cct cag tta cga ata ctg agc cat gag tcg gtt tgt    1104
Thr Ser Trp Ala Pro Gln Leu Arg Ile Leu Ser His Glu Ser Val Cys
        355                 360                 365 ggt ttc ttg act cat tgt ggt tct gga tca att gtg gaa ggg cta atg    1152
Gly Phe Leu Thr His Cys Gly Ser Gly Ser Ile Val Glu Gly Leu Met
    370                 375                 380 ttt ggt cac cct cta atc atg cta ccg att ttt ggg gac caa cct ctg    1200
Phe Gly His Pro Leu Ile Met Leu Pro Ile Phe Gly Asp Gln Pro Leu
385                 390                 395                 400 aat gct cga tta ctg gag gac aaa cag gtg gga atc gag ata cca aga    1248
Asn Ala Arg Leu Leu Glu Asp Lys Gln Val Gly Ile Glu Ile Pro Arg
                405                 410                 415
```

```
aat gag gaa gat ggt tgc ttg acc aag gag tcg gtt gct aga tca ctg     1296
Asn Glu Glu Asp Gly Cys Leu Thr Lys Glu Ser Val Ala Arg Ser Leu
            420                 425                 430 agg tcc gtt gtt gtg gaa aaa gaa ggg gag atc tac aag gcg aac gcg     1344
Arg Ser Val Val Val Glu Lys Glu Gly Glu Ile Tyr Lys Ala Asn Ala
        435                 440                 445 agg gag ctg agt aaa atc tat aac gac act aag gtt gaa aaa gaa tat     1392
Arg Glu Leu Ser Lys Ile Tyr Asn Asp Thr Lys Val Glu Lys Glu Tyr
    450                 455                 460 gta agc caa ttc gta gac tat ttg gaa aag aat gcg cgt gcg gtt gcc     1440
Val Ser Gln Phe Val Asp Tyr Leu Glu Lys Asn Ala Arg Ala Val Ala
465                 470                 475                 480 atc gat cat gag agt taa                                             1458
Ile Asp His Glu Ser
                485

<210> SEQ ID NO 2
<211> LENGTH: 485
<212> TYPE: PRT
<213> ORGANISM: Stevia rebaudiana

<400> SEQUENCE: 2

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Tyr Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr
                85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
        115                 120                 125

Trp Ile Ile Tyr Asp Tyr Thr His Tyr Trp Leu Pro Ser Ile Ala Ala
    130                 135                 140

Ser Leu Gly Ile Ser Arg Ala His Phe Ser Val Thr Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Leu Val
        195                 200                 205

Pro Tyr Lys Ala Pro Gly Ile Ser Asp Gly Tyr Arg Met Gly Leu Val
    210                 215                 220

Leu Lys Gly Ser Asp Cys Leu Leu Ser Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
            260                 265                 270
```

```
Thr Trp Val Ser Ile Lys Lys Trp Leu Asp Gly Lys Gln Lys Gly Ser
        275                 280                 285

Val Val Tyr Val Ala Leu Gly Ser Glu Val Leu Val Ser Gln Thr Glu
    290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
            340                 345                 350

Thr Ser Trp Ala Pro Gln Leu Arg Ile Leu Ser His Glu Ser Val Cys
        355                 360                 365

Gly Phe Leu Thr His Cys Gly Ser Gly Ser Ile Val Glu Gly Leu Met
    370                 375                 380

Phe Gly His Pro Leu Ile Met Leu Pro Ile Phe Gly Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Val Glu Lys Glu Gly Glu Ile Tyr Lys Ala Asn Ala
        435                 440                 445

Arg Glu Leu Ser Lys Ile Tyr Asn Asp Thr Lys Val Glu Lys Glu Tyr
    450                 455                 460

Val Ser Gln Phe Val Asp Tyr Leu Glu Lys Asn Ala Arg Ala Val Ala
465                 470                 475                 480

Ile Asp His Glu Ser
                485

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacccatatg tacaacgtta cttatcatca                                        30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggatccttaa ctctcatgat cgatggca                                          28

<210> SEQ ID NO 5
<211> LENGTH: 1446
<212> TYPE: DNA
<213> ORGANISM: Stevia rebaudiana
<220> FEATURE:
<221> NAME/KEY: CDS
<222> LOCATION: (1)..(1443)

<400> SEQUENCE: 5
```

-continued

| | |
|---|---|
| atg gat gca atg gct aca act gag aag aaa cca cac gtc atc ttc ata<br>Met Asp Ala Met Ala Thr Thr Glu Lys Lys Pro His Val Ile Phe Ile<br>1               5                   10                  15 | 48 |
| cca ttt cca gca caa agc cac att aaa gcc atg ctc aaa cta gca caa<br>Pro Phe Pro Ala Gln Ser His Ile Lys Ala Met Leu Lys Leu Ala Gln<br>            20                  25                  30 | 96 |
| ctt ctc cac cac aaa gga ctc cag ata acc ttc gtc aac acc gac ttc<br>Leu Leu His His Lys Gly Leu Gln Ile Thr Phe Val Asn Thr Asp Phe<br>        35                  40                  45 | 144 |
| atc cac aac cag ttt ctt gaa tca tcg ggc cca cat tgt cta gac ggt<br>Ile His Asn Gln Phe Leu Glu Ser Ser Gly Pro His Cys Leu Asp Gly<br>50                  55                  60 | 192 |
| tca ccg ggt ttc cgg ttc caa acc att ccg gat ggt gtt tct cac agt<br>Ser Pro Gly Phe Arg Phe Gln Thr Ile Pro Asp Gly Val Ser His Ser<br>65                  70                  75                  80 | 240 |
| ccg gaa gcg agc atc cca atc aga gaa tca ctc ttg aga tcc att gaa<br>Pro Glu Ala Ser Ile Pro Ile Arg Glu Ser Leu Leu Arg Ser Ile Glu<br>                85                  90                  95 | 288 |
| acc aac ttc ttg gat cgt ttc att gat ctt gta acc aaa ctt ccg gat<br>Thr Asn Phe Leu Asp Arg Phe Ile Asp Leu Val Thr Lys Leu Pro Asp<br>            100                 105                 110 | 336 |
| cct ccg act tgt att atc tca gat ggg ttc ttg tcg gtt ttc aca att<br>Pro Pro Thr Cys Ile Ile Ser Asp Gly Phe Leu Ser Val Phe Thr Ile<br>        115                 120                 125 | 384 |
| gac gct gca aaa aag ctt gga att ccg gtc atg atg tat tgg aca ctt<br>Asp Ala Ala Lys Lys Leu Gly Ile Pro Val Met Met Tyr Trp Thr Leu<br>130                 135                 140 | 432 |
| gct gcc tgt ggg ttc atg ggt ttt tac cat att cat tct ctc att gag<br>Ala Ala Cys Gly Phe Met Gly Phe Tyr His Ile His Ser Leu Ile Glu<br>145                 150                 155                 160 | 480 |
| aaa gga ttt gca cca ctt aaa gat gca agt tac ttg aca aat ggg tat<br>Lys Gly Phe Ala Pro Leu Lys Asp Ala Ser Tyr Leu Thr Asn Gly Tyr<br>                165                 170                 175 | 528 |
| ttg gac acc gtc att gat tgg gtt ccg gga atg gaa ggc atc cgt ctc<br>Leu Asp Thr Val Ile Asp Trp Val Pro Gly Met Glu Gly Ile Arg Leu<br>            180                 185                 190 | 576 |
| aag gat ttc ccg ctg gac tgg agc act gac ctc aat gac aaa gtt ttg<br>Lys Asp Phe Pro Leu Asp Trp Ser Thr Asp Leu Asn Asp Lys Val Leu<br>        195                 200                 205 | 624 |
| atg ttc act acg gaa gct cct caa agg tca cac acg gtt tca cat cat<br>Met Phe Thr Thr Glu Ala Pro Gln Arg Ser His Thr Val Ser His His<br>210                 215                 220 | 672 |
| att ttc cac acg ttc gat gag ttg gag cct agt att ata aaa act ttg<br>Ile Phe His Thr Phe Asp Glu Leu Glu Pro Ser Ile Ile Lys Thr Leu<br>225                 230                 235                 240 | 720 |
| tca ttg agg tat aat cac att tac acc atc ggc cca ctg caa tta ctt<br>Ser Leu Arg Tyr Asn His Ile Tyr Thr Ile Gly Pro Leu Gln Leu Leu<br>                245                 250                 255 | 768 |
| ctt gat caa ata ccc gaa gag aaa aag caa act gga att acg agt ctc<br>Leu Asp Gln Ile Pro Glu Glu Lys Lys Gln Thr Gly Ile Thr Ser Leu<br>            260                 265                 270 | 816 |
| cat gga tac agt tta gta aaa gaa gaa cca gag tgt ttc cag tgg ctt<br>His Gly Tyr Ser Leu Val Lys Glu Glu Pro Glu Cys Phe Gln Trp Leu<br>        275                 280                 285 | 864 |
| cag tct aaa gaa cca aat tcc gtc gtt tat gta aat ttt gga agt act<br>Gln Ser Lys Glu Pro Asn Ser Val Val Tyr Val Asn Phe Gly Ser Thr<br>290                 295                 300 | 912 |
| aca gta atg tct tta gaa gac atg acg gaa ttt ggt tgg gga ctt gct<br>Thr Val Met Ser Leu Glu Asp Met Thr Glu Phe Gly Trp Gly Leu Ala | 960 |

```
                305                 310                 315                 320
aat agc aac cat tat ttc ctt tgg atc atc cga tca aac ttg gtg ata         1008
Asn Ser Asn His Tyr Phe Leu Trp Ile Ile Arg Ser Asn Leu Val Ile
                325                 330                 335 ggg gaa aat gca gtt ttg ccc cct gaa ctt gag gaa cat ata aag aaa         1056
Gly Glu Asn Ala Val Leu Pro Pro Glu Leu Glu Glu His Ile Lys Lys
            340                 345                 350 aga ggc ttt att gct agc tgg tgt tca caa gaa aag gtc ttg aag cac         1104
Arg Gly Phe Ile Ala Ser Trp Cys Ser Gln Glu Lys Val Leu Lys His
                355                 360                 365 cct tcg gtt gga ggg ttc ttg act cat tgt ggg tgg gga tcg acc atc         1152
Pro Ser Val Gly Gly Phe Leu Thr His Cys Gly Trp Gly Ser Thr Ile
        370                 375                 380 gag agc ttg tct gct ggg gtg cca atg ata tgc tgg cct tat tcg tgg         1200
Glu Ser Leu Ser Ala Gly Val Pro Met Ile Cys Trp Pro Tyr Ser Trp
385                 390                 395                 400 gac cag ctg acc aac tgt agg tat ata tgc aaa gaa tgg gag gtt ggg         1248
Asp Gln Leu Thr Asn Cys Arg Tyr Ile Cys Lys Glu Trp Glu Val Gly
                405                 410                 415 ctc gag atg gga acc aaa gtg aaa cga gat gaa gtc aag agg ctt gta         1296
Leu Glu Met Gly Thr Lys Val Lys Arg Asp Glu Val Lys Arg Leu Val
            420                 425                 430 caa gag ttg atg gga gaa gga ggt cac aaa atg agg aac aag gct aaa         1344
Gln Glu Leu Met Gly Glu Gly Gly His Lys Met Arg Asn Lys Ala Lys
                435                 440                 445 gat tgg aaa gaa aag gct cgc att gca ata gct cct aac ggt tca tct         1392
Asp Trp Lys Glu Lys Ala Arg Ile Ala Ile Ala Pro Asn Gly Ser Ser
        450                 455                 460 tct ttg aac ata gac aaa atg gtc aag gaa atc acc gtg cta gca aga         1440
Ser Leu Asn Ile Asp Lys Met Val Lys Glu Ile Thr Val Leu Ala Arg
465                 470                 475                 480 aac tag                                                                  1446
Asn <210> SEQ ID NO 6
<211> LENGTH: 481
<212> TYPE: PRT
<213> ORGANISM: Stevia rebaudiana

<400> SEQUENCE: 6

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ser Pro Gly Phe Arg Phe Gln Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140
```

```
Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
            165                 170                 175

Leu Asp Thr Val Ile Asp Trp Val Pro Gly Met Glu Gly Ile Arg Leu
        180                 185                 190

Lys Asp Phe Pro Leu Asp Trp Ser Thr Asp Leu Asn Asp Lys Val Leu
    195                 200                 205

Met Phe Thr Thr Glu Ala Pro Gln Arg Ser His Thr Val Ser His His
210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn
```

<210> SEQ ID NO 7
<211> LENGTH: 1383
<212> TYPE: DNA
<213> ORGANISM: Stevia rebaudiana
<220> FEATURE:
<221> NAME/KEY: CDS
<222> LOCATION: (1)..(1380)

<400> SEQUENCE: 7

```
atg gcg gaa caa caa aag atc aag aaa tca cca cac gtt cta ctc atc    48
Met Ala Glu Gln Gln Lys Ile Lys Lys Ser Pro His Val Leu Leu Ile
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
cca ttc cct tta caa ggc cat ata aac cct ttc atc cag ttt ggc aaa      96
Pro Phe Pro Leu Gln Gly His Ile Asn Pro Phe Ile Gln Phe Gly Lys
             20                  25                  30 cga tta atc tcc aaa ggt gtc aaa aca aca ctt gtt acc acc atc cac     144
Arg Leu Ile Ser Lys Gly Val Lys Thr Thr Leu Val Thr Thr Ile His
             35                  40                  45 acc tta aac tca acc cta aac cac agt aac acc acc acc tcc atc        192
Thr Leu Asn Ser Thr Leu Asn His Ser Asn Thr Thr Thr Ser Ile
     50                  55                  60 gaa atc caa gca att tcc gat ggt tgt gat gaa ggc ggt ttt atg agt    240
Glu Ile Gln Ala Ile Ser Asp Gly Cys Asp Glu Gly Gly Phe Met Ser
 65                  70                  75                  80 gca gga gaa tca tat ttg gaa aca ttc aaa caa gtt ggg tct aaa tca    288
Ala Gly Glu Ser Tyr Leu Glu Thr Phe Lys Gln Val Gly Ser Lys Ser
                 85                  90                  95 cta gct gac tta atc aag aag ctt caa agt gaa gga acc aca att gat    336
Leu Ala Asp Leu Ile Lys Lys Leu Gln Ser Glu Gly Thr Thr Ile Asp
             100                 105                 110 gca atc att tat gat tct atg act gaa tgg gtt tta gat gtt gca att    384
Ala Ile Ile Tyr Asp Ser Met Thr Glu Trp Val Leu Asp Val Ala Ile
             115                 120                 125 gag ttt gga atc gat ggt ggt tcg ttt ttc act caa gct tgt gtt gta    432
Glu Phe Gly Ile Asp Gly Gly Ser Phe Phe Thr Gln Ala Cys Val Val
 130                 135                 140 aac agc tta tat tat cat gtt cat aag ggt ttg att tct ttg cca ttg    480
Asn Ser Leu Tyr Tyr His Val His Lys Gly Leu Ile Ser Leu Pro Leu
145                 150                 155                 160 ggt gaa act gtt tcg gtt cct gga ttt cca gag ctt caa cgg tgg gag    528
Gly Glu Thr Val Ser Val Pro Gly Phe Pro Glu Leu Gln Arg Trp Glu
                 165                 170                 175 aca ccg tta att ttg cag aat cat gag caa ata cag agc cct tgg tct    576
Thr Pro Leu Ile Leu Gln Asn His Glu Gln Ile Gln Ser Pro Trp Ser
             180                 185                 190 cag atg ttg ttt ggt cag ttt gct aat att gat caa gca cgt tgg gtc    624
Gln Met Leu Phe Gly Gln Phe Ala Asn Ile Asp Gln Ala Arg Trp Val
             195                 200                 205 ttc aca aat agt ttt tac aag ctc gag gaa gag gta ata gag tgg acg    672
Phe Thr Asn Ser Phe Tyr Lys Leu Glu Glu Glu Val Ile Glu Trp Thr
             210                 215                 220 aga aag ata tgg aac ttg aag gta atc ggg cca aca ctt cca tcc atg    720
Arg Lys Ile Trp Asn Leu Lys Val Ile Gly Pro Thr Leu Pro Ser Met
225                 230                 235                 240 tac ctt gac aaa cga ctt gat gat gat aaa gat aac gga ttt aat ctc    768
Tyr Leu Asp Lys Arg Leu Asp Asp Asp Lys Asp Asn Gly Phe Asn Leu
                 245                 250                 255 tac aaa gca aac cat cat gag tgc atg aac tgg tta gac gat aag cca    816
Tyr Lys Ala Asn His His Glu Cys Met Asn Trp Leu Asp Asp Lys Pro
             260                 265                 270 aag gaa tca gtt gtt tac gta gca ttt ggt agc ctg gtg aaa cat gga    864
Lys Glu Ser Val Val Tyr Val Ala Phe Gly Ser Leu Val Lys His Gly
             275                 280                 285 ccc gaa caa gtg gaa gaa atc aca cgg gct tta ata gat agt gat gtc    912
Pro Glu Gln Val Glu Glu Ile Thr Arg Ala Leu Ile Asp Ser Asp Val
 290                 295                 300 aac ttc ttg tgg gtt atc aaa cat aaa gaa gag gga aag ctc cca gaa    960
Asn Phe Leu Trp Val Ile Lys His Lys Glu Glu Gly Lys Leu Pro Glu
305                 310                 315                 320 aat ctt tcg gaa gta ata aaa acc gga aag ggt ttg att gta gca tgg   1008
```

```
Asn Leu Ser Glu Val Ile Lys Thr Gly Lys Gly Leu Ile Val Ala Trp
            325                 330                 335 tgc aaa caa ttg gat gtg tta gca cac gaa tca gta gga tgc ttt gtt      1056
Cys Lys Gln Leu Asp Val Leu Ala His Glu Ser Val Gly Cys Phe Val
            340                 345                 350 aca cat tgt ggg ttc aac tca act ctt gaa gca ata agt ctt gga gtc      1104
Thr His Cys Gly Phe Asn Ser Thr Leu Glu Ala Ile Ser Leu Gly Val
            355                 360                 365 ccc gtt gtt gca atg cct caa ttt tcg gat caa act aca aat gcc aag      1152
Pro Val Val Ala Met Pro Gln Phe Ser Asp Gln Thr Thr Asn Ala Lys
        370                 375                 380 ctt cta gat gaa att ttg ggt gtt gga gtt aga gtt aag gct gat gag      1200
Leu Leu Asp Glu Ile Leu Gly Val Gly Val Arg Val Lys Ala Asp Glu
385                 390                 395                 400 aat ggg ata gtg aga aga gga aat ctt gcg tca tgt att aag atg att      1248
Asn Gly Ile Val Arg Arg Gly Asn Leu Ala Ser Cys Ile Lys Met Ile
                405                 410                 415 atg gag gag gaa aga gga gta ata atc cga aag aat gcg gta aaa tgg      1296
Met Glu Glu Glu Arg Gly Val Ile Ile Arg Lys Asn Ala Val Lys Trp
            420                 425                 430 aag gat ttg gct aaa gta gcc gtt cat gaa ggt ggt agc tca gac aat      1344
Lys Asp Leu Ala Lys Val Ala Val His Glu Gly Gly Ser Ser Asp Asn
            435                 440                 445 gat att gtc gaa ttt gta agt gag cta att aag gct taa                  1383
Asp Ile Val Glu Phe Val Ser Glu Leu Ile Lys Ala
        450                 455                 460

<210> SEQ ID NO 8
<211> LENGTH: 460
<212> TYPE: PRT
<213> ORGANISM: Stevia rebaudiana

<400> SEQUENCE: 8

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Glu Leu Gln Arg Trp Glu
                165                 170                 175

Thr Pro Leu Ile Leu Gln Asn His Glu Gln Ile Gln Ser Pro Trp Ser
            180                 185                 190
```

-continued

```
Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460

<210> SEQ ID NO 9
<211> LENGTH: 1377
<212> TYPE: DNA
<213> ORGANISM: Stevia rebaudiana
<220> FEATURE:
<221> NAME/KEY: CDS
<222> LOCATION: (1)..(1374)

<400> SEQUENCE: 9 atg gaa aat aaa acg gag acc acc gtt cgc cgg cgc cgg aga ata ata    48
Met Glu Asn Lys Thr Glu Thr Thr Val Arg Arg Arg Arg Arg Ile Ile
1               5                   10                  15 tta ttc ccg gta cca ttt caa ggc cac att aac cca att ctt cag cta    96
Leu Phe Pro Val Pro Phe Gln Gly His Ile Asn Pro Ile Leu Gln Leu
            20                  25                  30 gcc aat gtg ttg tac tct aaa gga ttc agt atc acc atc ttt cac acc   144
Ala Asn Val Leu Tyr Ser Lys Gly Phe Ser Ile Thr Ile Phe His Thr
        35                  40                  45 aac ttc aac aaa ccc aaa aca tct aat tac cct cac ttc act ttc aga   192
Asn Phe Asn Lys Pro Lys Thr Ser Asn Tyr Pro His Phe Thr Phe Arg
    50                  55                  60 ttc atc ctc gac aac gac cca caa gac gaa cgc att tcc aat cta ccg   240
```

```
              Phe Ile Leu Asp Asn Asp Pro Gln Asp Glu Arg Ile Ser Asn Leu Pro
              65                  70                  75                  80 act cat ggt ccg ctc gct ggt atg cgg att ccg att atc aac gaa cac          288
Thr His Gly Pro Leu Ala Gly Met Arg Ile Pro Ile Ile Asn Glu His
                    85                  90                  95 gga gct gac gaa tta cga cgc gaa ctg gaa ctg ttg atg tta gct tct          336
Gly Ala Asp Glu Leu Arg Arg Glu Leu Glu Leu Leu Met Leu Ala Ser
                100                 105                 110 gaa gaa gat gaa gag gta tcg tgt tta atc acg gat gct ctt tgg tac          384
Glu Glu Asp Glu Glu Val Ser Cys Leu Ile Thr Asp Ala Leu Trp Tyr
                115                 120                 125 ttc gcg caa tct gtt gct gac agt ctt aac ctc cga ccg ctt gtt ttg          432
Phe Ala Gln Ser Val Ala Asp Ser Leu Asn Leu Arg Pro Leu Val Leu
            130                 135                 140 atg aca agc agc ttg ttt aat ttt cat gca cat gtt tca ctt cct cag          480
Met Thr Ser Ser Leu Phe Asn Phe His Ala His Val Ser Leu Pro Gln
145                 150                 155                 160 ttt gat gag ctt ggt tac ctc gat cct gat gac aaa acc cgt ttg gaa          528
Phe Asp Glu Leu Gly Tyr Leu Asp Pro Asp Asp Lys Thr Arg Leu Glu
                165                 170                 175 gaa caa gcg agt ggg ttt cct atg cta aaa gtg aaa gac atc aag tct          576
Glu Gln Ala Ser Gly Phe Pro Met Leu Lys Val Lys Asp Ile Lys Ser
                180                 185                 190 gcg tat tcg aac tgg caa ata ctc aaa gag ata tta ggg aag atg ata          624
Ala Tyr Ser Asn Trp Gln Ile Leu Lys Glu Ile Leu Gly Lys Met Ile
                195                 200                 205 aaa caa aca aaa gca tct tca gga gtc atc tgg aac tca ttt aag gaa          672
Lys Gln Thr Lys Ala Ser Ser Gly Val Ile Trp Asn Ser Phe Lys Glu
            210                 215                 220 ctc gaa gag tct gag ctc gaa act gtt atc cgt gag atc ccg gct cca          720
Leu Glu Glu Ser Glu Leu Glu Thr Val Ile Arg Glu Ile Pro Ala Pro
225                 230                 235                 240 agt ttc ttg ata cca ctc ccc aag cat ttg aca gcc tct tcc agc agc          768
Ser Phe Leu Ile Pro Leu Pro Lys His Leu Thr Ala Ser Ser Ser Ser
                245                 250                 255 tta cta gac cac gat cga acc gtt ttt caa tgg tta gac caa caa ccg          816
Leu Leu Asp His Asp Arg Thr Val Phe Gln Trp Leu Asp Gln Gln Pro
                260                 265                 270 cca agt tcg gta ctg tat gtt agt ttt ggt agt act agt gaa gtg gat          864
Pro Ser Ser Val Leu Tyr Val Ser Phe Gly Ser Thr Ser Glu Val Asp
            275                 280                 285 gag aaa gat ttc ttg gaa ata gct cgt ggg ttg gtt gat agc aag cag          912
Glu Lys Asp Phe Leu Glu Ile Ala Arg Gly Leu Val Asp Ser Lys Gln
290                 295                 300 tcg ttt tta tgg gtg gtt cga cct ggg ttt gtc aag ggt tcg acg tgg          960
Ser Phe Leu Trp Val Val Arg Pro Gly Phe Val Lys Gly Ser Thr Trp
305                 310                 315                 320 gtc gaa ccg ttg cca gat ggg ttc ttg ggt gaa aga gga cgt att gtg         1008
Val Glu Pro Leu Pro Asp Gly Phe Leu Gly Glu Arg Gly Arg Ile Val
                325                 330                 335 aaa tgg gtt cca cag caa gaa gtg cta gct cat gga gca ata ggc gca         1056
Lys Trp Val Pro Gln Gln Glu Val Leu Ala His Gly Ala Ile Gly Ala
            340                 345                 350 ttc tgg act cat agc gga tgg aac tct acg ttg gaa agc gtt tgt gaa         1104
Phe Trp Thr His Ser Gly Trp Asn Ser Thr Leu Glu Ser Val Cys Glu
                355                 360                 365 ggt gtt cct atg att ttc tcg gat ttt ggg ctc gat caa ccg ttg aat         1152
Gly Val Pro Met Ile Phe Ser Asp Phe Gly Leu Asp Gln Pro Leu Asn
370                 375                 380
```

```
gct aga tac atg agt gat gtt ttg aag gta ggg gtg tat ttg gaa aat    1200
Ala Arg Tyr Met Ser Asp Val Leu Lys Val Gly Val Tyr Leu Glu Asn
385                 390                 395                 400 ggg tgg gaa aga gga gag ata gca aat gca ata aga aga gtt atg gtg    1248
Gly Trp Glu Arg Gly Glu Ile Ala Asn Ala Ile Arg Arg Val Met Val
            405                 410                 415 gat gaa gaa gga gaa tac att aga cag aat gca aga gtt ttg aaa caa    1296
Asp Glu Glu Gly Glu Tyr Ile Arg Gln Asn Ala Arg Val Leu Lys Gln
        420                 425                 430 aag gca gat gtt tct ttg atg aag ggt ggt tcg tct tac gaa tca tta    1344
Lys Ala Asp Val Ser Leu Met Lys Gly Gly Ser Ser Tyr Glu Ser Leu
    435                 440                 445 gag tct cta gtt tct tac att tca tcg ttg taa                        1377
Glu Ser Leu Val Ser Tyr Ile Ser Ser Leu
    450                 455
```

<210> SEQ ID NO 10
<211> LENGTH: 458
<212> TYPE: PRT
<213> ORGANISM: Stevia rebaudiana

<400> SEQUENCE: 10

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Pro Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270
```

-continued

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
        290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacccatatg gatgcaatgg ctacaactga gaa                               33

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agatctctag tttcttgcta gcacggtgat tt                                32

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacccatatg gcggaacaac aaaagatcaa gaaat                             35

<210> SEQ ID NO 14
<211> LENGTH: 35
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 14
ggatccttaa gccttaatta gctcacttac aaatt                              35

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacccatatg gaaaataaaa cggagacca                                     29

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggatccttac aacgatgaaa tgtaagaaac ta                                 32

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acagatctat ggatgcaatg gctacaactg aga                                33

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagtcgacta gtttcttgct agcacggtga tttc                               34

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagcggccgc atgtacaacg ttacttatca tcaaaattca aa                      42

<210> SEQ ID NO 20
<211> LENGTH: 31
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 20
cgttaattaa ctctcatgat cgatggcaac c                                    31

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aagcggccgc atggcggaac aacaaaagat caag                                 34

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgttaattaa gccttaatta gctcacttac aaattcg                              37

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaggatccat ggaaaataaa acggagacca ccg                                  33

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcgtcgactt acaacgatga aatgtaagaa actagagact ctaa                      44

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caagtcccca accaaattcc gt                                              22

<210> SEQ ID NO 26
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 26
cacgaacccg tctggcaact c                                              21

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cccgtgtgat tcttccact tgttc                                           25

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caagaaccca tctggcaacg g                                              21

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gattattaaa cttctttgcg tccatcca                                       28

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctctatact ttaacgtcaa ggagaaaaaa cc                                  32

<210> SEQ ID NO 31
<211> LENGTH: 1422
<212> TYPE: DNA
<213> ORGANISM: Stevia rebaudiana
<220> FEATURE:
<221> NAME/KEY: CDS
<222> LOCATION: (1)..(1419)

<400> SEQUENCE: 31 atg gct acc agt gac tcc ata gtt gac gac cgt aag cag ctt cat gtt    48
Met Ala Thr Ser Asp Ser Ile Val Asp Asp Arg Lys Gln Leu His Val
 1               5                  10                  15 gcg acg ttc cca tgg ctt gct ttc ggt cac atc ctc cct tac ctt cag    96
Ala Thr Phe Pro Trp Leu Ala Phe Gly His Ile Leu Pro Tyr Leu Gln
                20                  25                  30 ctt tcg aaa ttg ata gct gaa aag ggt cac aaa gtc tcg ttt ctt tct   144
```

| | | |
|---|---|---|
| Leu Ser Lys Leu Ile Ala Glu Lys Gly His Lys Val Ser Phe Leu Ser<br>35                     40                    45 | | |
| acc acc aga aac att caa cgt ctc tct tct cat atc tcg cca ctc ata<br>Thr Thr Arg Asn Ile Gln Arg Leu Ser Ser His Ile Ser Pro Leu Ile<br>50                     55                   60 | | 192 |
| aat gtt gtt caa ctc aca ctt cca cgt gtc caa gag ctg ccg gag gat<br>Asn Val Val Gln Leu Thr Leu Pro Arg Val Gln Glu Leu Pro Glu Asp<br>65                     70                    75                    80 | | 240 |
| gca gag gcg acc act gac gtc cac cct gaa gat att cca tat ctc aag<br>Ala Glu Ala Thr Thr Asp Val His Pro Glu Asp Ile Pro Tyr Leu Lys<br>                   85                    90                    95 | | 288 |
| aag gct tct gat ggt ctt caa ccg gag gtc acc cgg ttt cta gaa caa<br>Lys Ala Ser Asp Gly Leu Gln Pro Glu Val Thr Arg Phe Leu Glu Gln<br>                  100                   105                   110 | | 336 |
| cac tct ccg gac tgg att att tat gat tat act cac tac tgg ttg cca<br>His Ser Pro Asp Trp Ile Ile Tyr Asp Tyr Thr His Tyr Trp Leu Pro<br>                  115                   120                   125 | | 384 |
| tcc atc gcg gct agc ctc ggt atc tca cga gcc cac ttc tcc gtc acc<br>Ser Ile Ala Ala Ser Leu Gly Ile Ser Arg Ala His Phe Ser Val Thr<br>        130                   135                   140 | | 432 |
| act cca tgg gcc att gct tat atg gga ccc tca gct gac gcc atg ata<br>Thr Pro Trp Ala Ile Ala Tyr Met Gly Pro Ser Ala Asp Ala Met Ile<br>145                   150                   155                   160 | | 480 |
| aat ggt tca gat ggt cga acc acg gtt gag gat ctc acg aca ccg ccc<br>Asn Gly Ser Asp Gly Arg Thr Thr Val Glu Asp Leu Thr Thr Pro Pro<br>                  165                   170                   175 | | 528 |
| aag tgg ttt ccc ttt ccg acc aaa gta tgc tgg cgg aag cat gat ctt<br>Lys Trp Phe Pro Phe Pro Thr Lys Val Cys Trp Arg Lys His Asp Leu<br>                  180                   185                   190 | | 576 |
| gcc cga ctg gtg cct tac aaa gct ccg ggg ata tct gat gga tac cgt<br>Ala Arg Leu Val Pro Tyr Lys Ala Pro Gly Ile Ser Asp Gly Tyr Arg<br>        195                   200                   205 | | 624 |
| atg ggg ctg gtt ctt aag gga tct gat tgt ttg ctt tcc aaa tgt tac<br>Met Gly Leu Val Leu Lys Gly Ser Asp Cys Leu Leu Ser Lys Cys Tyr<br>210                   215                   220 | | 672 |
| cat gag ttt gga act caa tgg cta cct ctt ttg gag aca cta cac caa<br>His Glu Phe Gly Thr Gln Trp Leu Pro Leu Leu Glu Thr Leu His Gln<br>225                   230                   235                   240 | | 720 |
| gta ccg gtg gtt ccg gtg gga tta ctg cca ccg gaa ata ccc gga gac<br>Val Pro Val Val Pro Val Gly Leu Leu Pro Pro Glu Ile Pro Gly Asp<br>                  245                   250                   255 | | 768 |
| gag aaa gat gaa aca tgg gtg tca atc aag aaa tgg ctc gat ggt aaa<br>Glu Lys Asp Glu Thr Trp Val Ser Ile Lys Lys Trp Leu Asp Gly Lys<br>                  260                   265                   270 | | 816 |
| caa aaa ggc agt gtg gtg tac gtt gca tta gga agc gag gtt ttg gtg<br>Gln Lys Gly Ser Val Val Tyr Val Ala Leu Gly Ser Glu Val Leu Val<br>        275                   280                   285 | | 864 |
| agc caa acc gag gtt gtt gag tta gca ttg ggt ctc gag ctt tct ggg<br>Ser Gln Thr Glu Val Val Glu Leu Ala Leu Gly Leu Glu Leu Ser Gly<br>        290                   295                   300 | | 912 |
| ttg cca ttt gtt tgg gct tat aga aaa cca aaa ggt ccc gcg aag tca<br>Leu Pro Phe Val Trp Ala Tyr Arg Lys Pro Lys Gly Pro Ala Lys Ser<br>305                 310                   315                   320 | | 960 |
| gac tcg gtg gag ttg cca gac ggg ttc gtg gaa cga act cgt gac cgt<br>Asp Ser Val Glu Leu Pro Asp Gly Phe Val Glu Arg Thr Arg Asp Arg<br>                  325                   330                   335 | | 1008 |
| ggg ttg gtc tgg acg agt tgg gca cct cag tta cga ata ctg agc cat<br>Gly Leu Val Trp Thr Ser Trp Ala Pro Gln Leu Arg Ile Leu Ser His<br>                  340                   345                   350 | | 1056 |

| | | |
|---|---|---|
| gag tcg gtt tgt ggt ttc ttg act cat tgt ggt tct gga tca att gtg<br>Glu Ser Val Cys Gly Phe Leu Thr His Cys Gly Ser Gly Ser Ile Val<br>355                        360                       365 | | 1104 |
| gaa ggg cta atg ttt ggt cac cct cta atc atg cta ccg att ttt ggg<br>Glu Gly Leu Met Phe Gly His Pro Leu Ile Met Leu Pro Ile Phe Gly<br>370                       375                      380 | | 1152 |
| gac caa cct ctg aat gct cga tta ctg gag gac aaa cag gtg gga atc<br>Asp Gln Pro Leu Asn Ala Arg Leu Leu Glu Asp Lys Gln Val Gly Ile<br>385                   390                     395                      400 | | 1200 |
| gag ata cca aga aat gag gaa gat ggt tgc ttg acc aag gag tcg gtt<br>Glu Ile Pro Arg Asn Glu Glu Asp Gly Cys Leu Thr Lys Glu Ser Val<br>                  405                      410                      415 | | 1248 |
| gct aga tca ctg agg tcc gtt gtt gtg gaa aaa gaa ggg gag atc tac<br>Ala Arg Ser Leu Arg Ser Val Val Val Glu Lys Glu Gly Glu Ile Tyr<br>420                       425                      430 | | 1296 |
| aag gcg aac gcg agg gag ctg agt aaa atc tat aac gac act aag gtt<br>Lys Ala Asn Ala Arg Glu Leu Ser Lys Ile Tyr Asn Asp Thr Lys Val<br>                  435                      440                      445 | | 1344 |
| gaa aaa gaa tat gta agc caa ttc gta gac tat ttg gaa aag aat gcg<br>Glu Lys Glu Tyr Val Ser Gln Phe Val Asp Tyr Leu Glu Lys Asn Ala<br>450                       455                      460 | | 1392 |
| cgt gcg gtt gcc atc gat cat gag agt taa<br>Arg Ala Val Ala Ile Asp His Glu Ser<br>465                     470 | | 1422 |

<210> SEQ ID NO 32
<211> LENGTH: 473
<212> TYPE: PRT
<213> ORGANISM: Stevia rebaudiana

<400> SEQUENCE: 32

Met Ala Thr Ser Asp Ser Ile Val Asp Asp Arg Lys Gln Leu His Val
1                 5                   10                 15

Ala Thr Phe Pro Trp Leu Ala Phe Gly His Ile Leu Pro Tyr Leu Gln
                20                   25                   30

Leu Ser Lys Leu Ile Ala Glu Lys Gly His Lys Val Ser Phe Leu Ser
        35                      40                   45

Thr Thr Arg Asn Ile Gln Arg Leu Ser Ser His Ile Ser Pro Leu Ile
50                      55                   60

Asn Val Val Gln Leu Thr Leu Pro Arg Val Gln Glu Leu Pro Glu Asp
65                 70                   75                   80

Ala Glu Ala Thr Thr Asp Val His Pro Glu Asp Ile Pro Tyr Leu Lys
                85                   90                   95

Lys Ala Ser Asp Gly Leu Gln Pro Glu Val Thr Arg Phe Leu Glu Gln
        100                   105               110

His Ser Pro Asp Trp Ile Ile Tyr Asp Tyr Thr His Tyr Trp Leu Pro
        115                   120               125

Ser Ile Ala Ala Ser Leu Gly Ile Ser Arg Ala His Phe Ser Val Thr
130                    135                   140

Thr Pro Trp Ala Ile Ala Tyr Met Gly Pro Ser Ala Asp Ala Met Ile
145                 150                  155                 160

Asn Gly Ser Asp Gly Arg Thr Thr Val Glu Asp Leu Thr Thr Pro Pro
                165                   170               175

Lys Trp Phe Pro Phe Pro Thr Lys Val Cys Trp Arg Lys His Asp Leu
        180                   185               190

Ala Arg Leu Val Pro Tyr Lys Ala Pro Gly Ile Ser Asp Gly Tyr Arg
        195                   200               205

Met Gly Leu Val Leu Lys Gly Ser Asp Cys Leu Leu Ser Lys Cys Tyr
210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
            245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
            275                 280                 285

Ser Gln Thr Glu Val Val Glu Leu Ala Leu Gly Leu Glu Leu Ser Gly
290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
            325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
            355                 360                 365

Glu Gly Leu Met Phe Gly His Pro Leu Ile Met Leu Pro Ile Phe Gly
370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
            405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Glu Lys Asn Ala
            450                 455                 460

Arg Ala Val Ala Ile Asp His Glu Ser
465                 470

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgccgcgcg gcagccatat ggctaccagt gactccatag                          40

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctttgttagc agccggatcc ttaactctca tgatcgatgg caac                     44

<210> SEQ ID NO 35

```
<211> LENGTH: 33
<212> TYPE: PRT
<213> ORGANISM: Stevia rebaudiana

<400> SEQUENCE: 35

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp

<210> SEQ ID NO 36
<211> LENGTH: 21
<212> TYPE: PRT
<213> ORGANISM: Stevia rebaudiana

<400> SEQUENCE: 36

Met Ala Thr Ser Asp Ser Ile Val Asp Asp Arg Lys Gln Leu His Val
1               5                   10                  15

Ala Thr Phe Pro Trp
            20
```